US010098886B2

(12) United States Patent
Carra et al.

(10) Patent No.: US 10,098,886 B2
(45) Date of Patent: Oct. 16, 2018

(54) CRYSTALLINE FORMS OF (2R,5S,13AR)-8-HYDROXY-7,9-DIOXO-N-(2,4,6-TRIFLUORO-BENZYL)-2,3,4,5,7,9,13,13A-OCTAHYDRO-2,5-METHANOPYRIDO[1',2':4,5]PYRAZINO[2,1-B] [1,3] OXAZEPINE-10-CARBOXAMIDE

(71) Applicant: Gilead Sciences, Inc., Foster City, CA (US)

(72) Inventors: Ernest A. Carra, Foster City, CA (US); Irene Chen, San Mateo, CA (US); Katie Ann Keaton, Burlingame, CA (US); Scott E. Lazerwith, Burlingame, CA (US); Vahid Zia, Palo Alto, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/588,346

(22) Filed: May 5, 2017

(65) Prior Publication Data
US 2017/0333438 A1 Nov. 23, 2017

Related U.S. Application Data

(62) Division of application No. 14/745,121, filed on Jun. 19, 2015, now Pat. No. 9,682,084.

(60) Provisional application No. 62/017,183, filed on Jun. 25, 2014, provisional application No. 62/015,238, filed on Jun. 20, 2014.

(51) Int. Cl.
| C07D 498/18 | (2006.01) |
| A61K 31/5365 | (2006.01) |
| A61K 45/06 | (2006.01) |
| A61K 9/20 | (2006.01) |
| C07D 498/14 | (2006.01) |
| A61K 31/513 | (2006.01) |
| A61K 31/553 | (2006.01) |
| A61K 31/675 | (2006.01) |
| A61K 31/683 | (2006.01) |
| A61K 31/537 | (2006.01) |

(52) U.S. Cl.
CPC ............ *A61K 31/5365* (2013.01); *A61K 9/20* (2013.01); *A61K 31/513* (2013.01); *A61K 31/553* (2013.01); *A61K 31/675* (2013.01); *A61K 31/683* (2013.01); *A61K 45/06* (2013.01); *C07D 498/14* (2013.01); *C07D 498/18* (2013.01); *A61K 31/537* (2013.01); C07B 2200/13 (2013.01); Y02A 50/395 (2018.01)

(58) Field of Classification Search
CPC ............................ C07D 498/18; A61K 31/5365
USPC ................................. 544/95; 514/230.2
See application file for complete search history.

(56) References Cited

U.S. PATENT DOCUMENTS

| 5,814,639 A | 9/1998 | Liotta et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,620,841 B1 | 9/2003 | Fujishita et al. |
| 6,642,245 B1 | 11/2003 | Liotta et al. |
| 6,703,396 B1 | 3/2004 | Liotta et al. |
| 7,176,220 B2 | 2/2007 | Satoh et al. |
| 7,419,969 B2 | 9/2008 | Naidu et al. |
| 7,550,463 B2 | 6/2009 | Yoshida |
| 7,635,704 B2 | 12/2009 | Satoh et al. |
| 7,858,788 B2 | 12/2010 | Yoshida et al. |
| 8,129,385 B2 | 3/2012 | Johns et al. |
| 8,148,374 B2 | 4/2012 | Desai et al. |
| 8,188,271 B2 | 5/2012 | Yoshida et al. |
| 8,410,103 B2 | 4/2013 | Johns et al. |
| 8,592,397 B2 | 11/2013 | Dahl et al. |
| 8,633,219 B2 | 1/2014 | Matsuzaki et al. |
| 8,716,264 B2 | 5/2014 | Dahl et al. |
| 8,778,943 B2 | 7/2014 | Johns et al. |
| 8,981,103 B2 | 3/2015 | Ando et al. |
| 8,987,441 B2 | 3/2015 | Takahashi et al. |
| 9,051,337 B2 | 6/2015 | Johns et al. |
| 9,216,996 B2 | 12/2015 | Jin et al. |
| 9,682,084 B2 * | 6/2017 | Carra ................. A61K 31/5365 |
| 9,708,342 B2 | 7/2017 | Carra et al. |
| 2005/0054645 A1 | 3/2005 | Miyazaki et al. |
| 2005/0137224 A1 | 6/2005 | Shima et al. |
| 2007/0072831 A1 | 3/2007 | Cai et al. |
| 2007/0117848 A1 | 5/2007 | Puerta et al. |
| 2008/0020010 A1 | 1/2008 | Nair et al. |
| 2008/0139579 A1 | 6/2008 | Morrissette et al. |
| 2008/0161271 A1 | 7/2008 | Yoshida et al. |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318702 A1 | 12/2009 | Matsuda et al. |

(Continued)

FOREIGN PATENT DOCUMENTS

| DE | 2244012 A1 | 3/1973 |
| DE | 2552871 A1 | 7/1976 |

(Continued)

OTHER PUBLICATIONS

Agrawal, et al. (2012) "Probing Chelation Motifs in HIV Integrase Inhibitors" Proc. Natl. Acad. Sci. U.S.A.; 109(7): 2251-2256.

(Continued)

*Primary Examiner* — Kahsay Habte

(57) ABSTRACT

The present invention relates to crystalline forms and co-crystals of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, the pharmaceutical formulations, and the therapeutic uses thereof. The present invention also relates to novel crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

19 Claims, 16 Drawing Sheets

(56) References Cited

U.S. PATENT DOCUMENTS

| | | |
|---|---|---|
| 2010/0068695 A1 | 3/2010 | Kiyama et al. |
| 2012/0022251 A1 | 1/2012 | Sumino et al. |
| 2012/0108564 A1 | 5/2012 | Miyazaki et al. |
| 2012/0232117 A1 | 9/2012 | Bae et al. |
| 2014/0011995 A1 | 1/2014 | Sumino et al. |
| 2014/0094605 A1 | 4/2014 | Yoshida et al. |
| 2014/0221355 A1 | 8/2014 | Lazerwith et al. |
| 2014/0221356 A1 | 8/2014 | Jin et al. |
| 2014/0221378 A1 | 8/2014 | Miyazaki et al. |
| 2014/0243521 A1 | 8/2014 | Yoshida et al. |
| 2014/0256937 A1 | 9/2014 | Akiyama |
| 2015/0232479 A1 | 8/2015 | Johns et al. |
| 2018/0065986 A1 | 3/2018 | Carra et al. |

FOREIGN PATENT DOCUMENTS

| | | |
|---|---|---|
| DE | 2658401 A1 | 7/1978 |
| EP | 0154199 A2 | 9/1985 |
| EP | 0378067 A2 | 7/1990 |
| EP | 0456073 A2 | 11/1991 |
| EP | 1422218 A1 | 5/2004 |
| EP | 1544199 A1 | 6/2005 |
| EP | 1874117 A1 | 1/2008 |
| EP | 2412709 A1 | 2/2012 |
| EP | 2465580 A1 | 6/2012 |
| EP | 2527007 A1 | 11/2012 |
| EP | 2602260 A1 | 6/2013 |
| GB | 2345058 A | 6/2000 |
| WO | WO-1994/017090 A1 | 8/1994 |
| WO | WO-1999/005142 A1 | 2/1999 |
| WO | WO-1999/025345 A1 | 5/1999 |
| WO | WO-2000/027823 A1 | 5/2000 |
| WO | WO-2003/030897 A1 | 4/2003 |
| WO | WO-2003/035077 A1 | 5/2003 |
| WO | WO-2004/004657 A2 | 1/2004 |
| WO | WO-2004/024078 A2 | 3/2004 |
| WO | WO-2005/016927 A1 | 2/2005 |
| WO | WO-2005/042533 A2 | 5/2005 |
| WO | WO-2005/074513 A2 | 8/2005 |
| WO | WO-2005/110399 A2 | 11/2005 |
| WO | WO-2005/110414 A2 | 11/2005 |
| WO | WO-2005/112930 A1 | 12/2005 |
| WO | WO-2005/113508 A1 | 12/2005 |
| WO | WO-2005/113509 A1 | 12/2005 |
| WO | WO-2006/028523 A2 | 3/2006 |
| WO | WO-2006/030807 A1 | 3/2006 |
| WO | WO-2006/066414 A1 | 6/2006 |
| WO | WO-2006/088173 A1 | 8/2006 |
| WO | WO-2006/116764 A1 | 11/2006 |
| WO | WO-2007/014352 A2 | 2/2007 |
| WO | WO-2007/049675 A1 | 5/2007 |
| WO | WO-2007/079260 A1 | 7/2007 |
| WO | WO-2007/089030 A1 | 8/2007 |
| WO | WO-2007/092681 A2 | 8/2007 |
| WO | WO-2007/102499 A1 | 9/2007 |
| WO | WO-2007/102512 A1 | 9/2007 |
| WO | WO-2008/002959 A2 | 1/2008 |
| WO | WO-2008/033836 A2 | 3/2008 |
| WO | WO-2008/048538 A1 | 4/2008 |
| WO | WO-2009/006119 A1 | 1/2009 |
| WO | WO-2009/006203 A1 | 1/2009 |
| WO | WO-2009/018320 A1 | 2/2009 |
| WO | WO-2009/018350 A1 | 2/2009 |
| WO | WO-2009/036161 A1 | 3/2009 |
| WO | WO-2009/103950 A1 | 8/2009 |
| WO | WO-2010/011812 A1 | 1/2010 |
| WO | WO-2010/011813 A1 | 1/2010 |
| WO | WO-2010/011814 A1 | 1/2010 |
| WO | WO-2010/011815 A1 | 1/2010 |
| WO | WO-2010/011816 A1 | 1/2010 |
| WO | WO-2010/011818 A1 | 1/2010 |
| WO | WO-2010/011819 A1 | 1/2010 |
| WO | WO-2010/068253 A1 | 6/2010 |
| WO | WO-2010/068262 A1 | 6/2010 |
| WO | WO-2010/110231 A1 | 9/2010 |
| WO | WO-2010/110409 A1 | 9/2010 |
| WO | WO-2010/147068 A1 | 12/2010 |
| WO | WO-2011/094150 A1 | 8/2011 |
| WO | WO-2011/105590 A1 | 9/2011 |
| WO | WO-2011/119566 A1 | 9/2011 |
| WO | WO-2012/009009 A2 | 1/2012 |
| WO | WO-2012/018065 A1 | 2/2012 |
| WO | WO-2012/039414 A1 | 3/2012 |
| WO | WO-2012/106534 A2 | 8/2012 |
| WO | WO-2012/151361 A1 | 11/2012 |
| WO | WO-2012/151567 A1 | 11/2012 |
| WO | WO-2013/038407 A1 | 3/2013 |
| WO | WO-2013/054862 A1 | 4/2013 |
| WO | WO-2013/087581 A1 | 6/2013 |
| WO | WO-2014/008636 A1 | 1/2014 |
| WO | WO-2014/011769 A1 | 1/2014 |
| WO | WO-2014/014933 A1 | 1/2014 |
| WO | WO-2014/018449 A1 | 1/2014 |
| WO | WO-2014/022707 A1 | 2/2014 |
| WO | WO-2014/074675 A1 | 5/2014 |
| WO | WO-2014/093941 A1 | 6/2014 |
| WO | WO-2014/099586 A1 | 6/2014 |
| WO | WO-2014/100077 A1 | 6/2014 |
| WO | WO-2014/100323 A1 | 6/2014 |
| WO | WO-2014/104279 A1 | 7/2014 |
| WO | WO-2014/200880 A1 | 12/2014 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |
| WO | WO-2015/110897 A2 | 7/2015 |

OTHER PUBLICATIONS

AIDS treatment Guidelines (2013)—"AIDS info Guidelines for the Use of Antiretroviral Agents in HIV-1-Infected Adults and Adolescents," [downloaded from http://aidsinfo.nih.gov/guidelines on Mar. 15, 2013], 267 pages.

Akiyama, et al. (2013) "Discovery of Novel HIV Integrase Inhibitors Part 2. Selection and Evaluation of an Azabicylic Carbamoyl Pyridone as apre-Clinical Candidate" Poster, American Chemical Society National Meeting and Exposition; Apr. 7-11; New Orleans, LA.

Andrews, C. et al. (2014) "Long-Acting Integrase Inhibitor Protects Macaques from Intrarectal Simian/Human Immunodeficiency Virus," Science 343:1151-1154.

Atsushi M. et al. (2001) "Regioselective Oxygenations of S—Trans Dienes, Silyl Dienol Ethers (SDEs), by Triphenyl Phosphite Ozonide (TPPO) and It's Mechanistic Study" The Journal of Organic Chemistry 66(10): 3548-3553.

Barrow J. C. et al (2000) "Preparation and Evaluation of 1, 3-diaminocyclopentane-linked dihydropyrimidinone derivatives as selective alphala-receptor antagonists" Bioorganic & Medicinal Chemistry Letters, Pergamon, Amsterdam, NL 10(17): 1917-1920.

Bisel, P. et al. (1998) "Diastereoselective .alpha.-iminoamine rearrangement: asymmetric synthesis of (R)-(−)- and (5)-(−)-2-benzyl-2-hydroxycyclohexanone" Tetrahedron: Asymmetry 9:4027-4034.

Brehm et. al. (1954) "The Relative Acidifying Influence of Oxygen and Sulfur Atoms on α—Hydrogen Atoms" 76:5389-5391.

Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6, 2013; Atlanta, GA.

Brocklehurst C.E. et al. (2011) "Diastereoisomeric Salt Formation and Enzyme-Catalyzed Kinetic Resolution as Complementary Methods for the Chiral Separation of cis -/ trans—Enantiomers of 3-Aminocyclohexanol" Organic Process Research and Development, 15(1): 294-300.

Cahn, P. et al. (2013) "Dolutegravir (DTG) is Superior to Raltegravir (RAL) in Art-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.

(56) References Cited

OTHER PUBLICATIONS

Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.

Castagna, A. et al. (2014) "Dolutegravir in Antiretroviral-Experienced Patients With Raltegravir-and/or Elvitegravir-Resistant HIV-1: 24-Week Results of the Phase III VIKING-3 Study" Infectious Diseases Society of America Journal of InfectiousDiseases 210:354-62.

Castellino, S., et al., (2013), "Metabolism, Excretion, and Mass Balance of the HIV-1 Integrase Inhibitor Dolutegravir in Humans", Antimicrobial Agents and Chemother., 57:3536-46.

Chen, D. et al. (2003) "New C19-diterpenoid alkaloids from the roots of Aconitum transsecutum" Abstract, Huaxue Xuebao 61(6):901-906.

Chen, S. et al. (2014) "Evaluation of the effect of UGT1A1 polymorphisms on dolutegravir pharmacokinetics" Pharmacogenomics, 15(1):9-16.

Chorell, E et al. (2012) "Design and Synthesis of Fluorescent Pilicides and Curlicides: Bioactive Tools to Study Bacterial Virulence Mechanisms" Chemistry—A European Journal, 18(15): 4522-4532.

Clotet, G. et al. (2014) "Once-daily dolutegravir versus darunavir plus ritonavir in antiretroviral-naive adults with HIV-1 infection (FLAMINGO) 48 week results from the randomised open-label phase 3b study", Lancet, 383:2222-31.

Cohen, J. et al. (2014) "A Bid to Thwart HIV With Shot of Long-Lasting Drug" Science 343:1067.

Cottrell, M. et al. (2013) "Clinical Pharmacokinetic, Pharmacodynamic and Drug-Interaction Profile of the Integrase Inhibitor Dolutegravir" Clin Pharmacokinet 52:981-994.

Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.

Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and SINGLE (ING114467)" Poster No. CUPE 282, 7.sup.th IAS Conference on HIV Pathogenesis, Treatment and Prevention; Jun. 30-Jul. 3; Kuala Lumpur, Malaysia.

Dauvergne J. et al. (2004) "Synthesis of 4-azacyclopent-2-enones and 5,5-dialkyl-4-azacyclopent-2-enones" Tetrahedron, Elsevier Science Publishers 60(11): 2559-2567.

Deanda, F. et al. (2013) "Dolutegravir Interactions with HIV-1 Integrase-DNA: Structural Rationale for Drug Resistance and Dissociation Kinetics" PLOS One 8(10): e77448 1-12.

Disclosed Anonymously. (2014) "Preparation of Methyl 3-(benzyloxy)-5-992,4-difluorobenzyl)carbamoyl)-1-(2,2-dimethoxy ethyl)-4-oxo1,4-dihydropyridine-2-carboxylate" An IP.com Prior Art Database Technical Disclosure, the whole document.

Disclosed Anonymously. (2014) "Process for the Preparation of 4H-PYRAN-4-ONE Derivatives" An IP.com Prior Art Database Technical Disclosure, //priorart.ip.com/IPCOM/000235923.

Enright, B. et al. (2010) "Assessment of Hydroxypropyl Methylcellulose, Propylene Glycol, Polysorbate 80, and Hydroxypropyl-.beta.-Cyclodextrin for Use in Developmental and Reproductive Toxicology Studies" Birth Defects Research (Part B) 89:504-516.

European Search Report dated Mar. 31, 2015 for EP application No. 13815937.1.

FDA DTG Pharmacology Review—Center for Drug Evaluation and Research; DTG PharmTox Review 2013, 103 pages.

FDA_DDI Guidance for Industry—Drug Interaction Studies—Study Design, Data Analysis, Implications for Dosing, and Labeling Recommendations, 79 pages.

Feinberg, J. et al. (2013) "Once-Daily Dolutegravir (DTG) is Superior to Darunavir/Ritonavir (DRV)/f) in Antiretroviral-Naive Adults: 48 Week Results from FLAMINGO (ING114915)" Presentation, 53.sup.rd ICAAC Interscience Conference on AntimicrobialAgents and Chemotherapy; Sep. 10-13; Denver CO.

Gad, S. et al. (2006) "Nonclinical Vehicle Use in Studies by Multiple Routes in Multiple Species" International Journal of Toxicology 25:499-521.

Gao, Y. et al. (2007) "Attenuating Pregnane X Receptor (PXR Activiatin: A Molecular Modeling Approach" Xenobiotica 37(2):124-138.

Gein, V. L., et al. (1992) "Synthesis of 4-Substituted 1-Methyl-5-Aryl- and 1,5-Diaryltetrahydropyrrole-2,3-Diones and their Antiviral Action" translated from Khimik-farmatsevticheskii Zhumal; 25(12):37-40.

Gould, S. et al. (2005) "2-Hydroxypropyl-.beta.-cyclodextrin (HP-.beta.-CD): A toxicology review" Food and Chemical Toxicology 43:1451-1459.

Gouverneur, V. et al. (1998) "New Acylnitroso Compounds for the Asymmetric Oxyamination of Dienes" Tetrahedron 54:10537-10554.

Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.

Gutierrez, M., "Drug safety profile of integrase strand transfer inhibitors," Expert Opin. Drug Saf. (2014) 13(4):431-445.

Hare, S. et al. (2011) "Structural and Functional Analyses of the Second-Generation Integrase Strand Transfer Inhibitor Dolutegravir (S/GSK1349572)" Molecular Pharmacology 80(4):565-572.

Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).

Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.

Hurt et al., (2014), "Resistance to HIV Integrase Strand Transfer Inhibitors Among Clinical Specimens in the United States, 2009-2012", Clin Infect Dis., 58:423-31.

Hurt, C. et al. (2013) "Characterization of Resistance to Integrase Strand Transfer Inhibitors among Clinical Specimens in the United States, 2009-2012" Poster 591; 20th Conference on Retroviruses and Opportunistic Infections; Mar. 3-6; Atlanta, GA.

International Preliminary Report on Patentability dated Jun. 23, 2015 for PCT/US2013/076367.

Intl Search Report—Written Opinion dated Sep. 18, 2006 for PCT/US2006/016604.

Intl. Search Report—Written Opinion dated Feb. 9, 2016 for PCT/US2015/026017.

Intl. Search Report dated Mar. 12, 2014 for PCT/US2013/076367.

Johns, B. et al.,(2013), "HIV Integrase Inhibitors", Successful Strategies for Discovery of Antiviral Drugs, 32(6):149-88.

Johns, B., et al., "Carbamoyl Pyridone HIV-1 Integrase Inhibitors 3. A Diastereomeric Approach to Chiral Nonracemic Tricyclic Ring Systems and the Discovery of S/GSK1349572 (Dolutegravir) and S/GSK1265744," J. Med. Chem. 54 pages.

Johns, B., et al., "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)," J. Med. Chem. (2013) 56:5901?5916 (16 pages).

Johns, B., et al., "Discovery of S/GSK1349572: A Once Daily Next Generation Integrase Inhibitor with a Superior Resistance Profile," 17th Conference on Retroviruses and Opportunistic Infections Feb. 16-19, 2010, San Francisco, CA, USA (18 pages).

Kawasuji, T., et al. (2007) "3-Hydroxy-1,5-dihydro-pyrrol-2-one Derivatives as Advanced Inhibitors of HIV Integrase" Bioorganic & Medicinal Chemistry; 15:5487-5492.

Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.

Kliewer, S. et al. (2002) "The Nuclear Pregnane X Receptor: A Key Regulator of Xenobiotic Metabolism" Endocrine Reviews 23(5):687-702.

(56) References Cited

OTHER PUBLICATIONS

Kobayashi, M. et al. (2011) "In Vitro Antiretroviral Properties of S/GSK1349572, a Next-Generation HIV Integrase Inhibitor" Antimicrob Agents and Chemother 55(2):813-21.
Krow et al., "Selectfluor as a Nucleofuge in the Reactions of Azabicyclo[n.2.1]alkane β-Halocarbamic Acid Esters (n=2,3)," J. Org. Chem. (2008) 73, 2122-2129.
Lepist, et al., Effect of Cobicistat and Ritonavir on Proximal Renal Tubular Cell Uptake and Efflux Tansporters, Poster No. A1-1724 (2011).
Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.
Llyod J. et al. (2009) "Dihydropyrazolopyrimidines containing benzimidazoles as KV1.5 potassium channel antagonistics" Bioorganic & Medicinal Chemistry Letters 19(18): 5469-5473.
Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference on Antimicrobial Agents and Chemotherapy; Sep. 10-13; Denver, CO.
Maggi, P., (2014) "The Problem of Renal Function Monitoring in Patients Treated With the Novel Antiretroviral Drugs", HIV Clinical Trials, HIV Clin Trials;15(3):87-91.
Malet, I., et al., (2014) "New raltegravir resistance pathways induce broad cross-resistance to all currently used integrase inhibitors", J Antimicrob Chemother, 69: 2118-2122.
Margolis et al. (2014) "744 and Rilpivirine as Two Drug Oral Maintenance Therapy: LAI116482 (LATTE) Week 48 Results" Presentation; 21st Conference on Retroviruses and Opportunistic Infections; Mar. 3-6; Boston, MA.
Menendez-Arias, L., Alvarez, M., "Antiretroviral therapy and drug resistance in human immunodeficiency virus type 2 infection," Antiviral Res. (2013), http://dx.doi.org/10.1016/j.antiviral.2013.12.001.
Metifiot, M. et al. (2013) "HIV Integrase Inhibitors: 20-Year Landmark and Challenges" Advances in Pharmacology 67:75-105.
Min, S. et al. (2010) "Pharmacokinetics and Safety of S/GSK1349572, a Next-Generation HIV Integrase Inhibitor, in Healthy Volunteers" Antimicrob Agents and Chemother 54(1):254-258.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Mulvihill M.J. et al. (1998) "Enzymatic resolution of aminocyclopentenols as precursors to D-and L-carbocyclic nucleosides" The Journal of Organic Chemistry, American Chemistry Society, US, 63(10): 3357-3363.
Nair, V. et al. (2014) "Pharmacokinetics and Dose-range Finding Toxicity of a Novel anti-HIV Active Integrase Inhibitor" Antiviral Research, 108:25-29.
Nair, V. et al. (2014) "Pharmacokinetics and Dose-range Finding Toxicity of a Novel anti-HIV Active Integrase Inhibitor" Supplementary Materials.
Nichols, G. et al (2013) "Phase 3 Assessment of Dolutegravir (DTG) 50 mg Twice Daily (BID) in HIV-1--Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.
Nichols, G. et al. (2012) "Antiviral Activity of Dolutegravir in Subjects With Failure on an Integrase Inhibitor-Based Regimen: Week 24 Phase 3 Results From VIKING-3" Presentation O232; 11th International Congress on Drug Therapy in HIV Infection;Nov. 11-15; Glasgow, UK.
Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.
Office Action dated Mar. 30, 2015 for Pakistan Appl. No. 908/2013.
Opposition Decision in European patent application No. 02749384.0, dated Mar. 12, 2015.
Pace, P., et al. (2007) "Dihydroxypyrimidine-4-carboxamides as Novel Potent and Selective HIV Integrase Inhibitors" J. Med. Chem; 50:2225-2239.
Park, B. et al. (2001) "Metabolism of Fluorine-Containing Drugs" Annu. Rev. Pharmacol. Toxicol. 41:443-70.
Patel, P. et al. (2014) "Relative Bioavailability of a Paediatric Granule Formulation of the HIV Integrase Inhibitor, Dolutegravir, in Healthy Adult Subjects" Antiviral Therapy.
Patel, P., et al., "Pharmacokinetics of the HIV integrase inhibitor S/GSK1349572 co-administered with acid-reducing agents and multivitamins in healthy volunteers," J Antimicrob Chemother (2011); 66: 1567-1572.
Peng, et al., "Norditerpenoid alkaloids from the roots of Aconitum hemsleyanum Pritz. var. pengzhouense," Chinese Chemical Letters, vol. 13, Issue: 3, pp. 233-236 (2002), Abstract.
Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.
Plamen A. et al. (2012) "Biomimetic Synthesis, antibacterial activity and structure-activity properties of the pyroglutamate core of oxazolomycin" Organic & Biomolecular Chemistry, 10(17): 3472-3485.
Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar. 3-6; Atlanta, GA.
Quashie, P. et al. (2013) "Evolution of HIV integrase resistance mutations" Curr Opin Infect Dis 26:43-49.
Raffi, F. et al. (2012) "Once-daily Dolutegravir (DTG; S/GSK1349572) is Non-inferior to Raltegravir (RAL) in Antiretroviral-naive Adults. 48 Week Results from SPRING-2 (ING113086)" Presentation THLBB04; XIX International AIDS Conference; Jul. 22-27;Washington, DC.
Raffi, F. et al. (2013) "Dolutegravir is Non-Inferior to Raltegravir and Shows Durable Response Through 96 Weeks: Results From the SPRING-2 Trial" Poster TULBPE17; 7.sup.th IAS Conference on HIV Pathogenesis, Treatment and Prevention; Jun. 30-Jul.3; Kuala Lumpur, Malaysia.
Raffi, F. et al. (2013) "Once-daily dolutegravir versus twice-daily raltegravir in antiretroviral-naive adults with HIV-1 infection (SPRING-2 study): 96 week results from a randomised, double-blind, non-inferiority trial" www.thelancet.com/infection13:927-935.
Raffi_Poster_DTG clinical data summary IAS Kuala Lumpur Jul. 2013 (Spring 2), 1 page.
Ragan, J. et al. (1995) "Studies of the Alkylation of Chiral, Non-Racemic, Tricyclic Pyrrolidinones," Heterocycles 41:57-70.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M., et al., "Assessing a Theoretical Risk of Dolutegravir-Induced Developmental Immunotoxicity in Juvenile Rats,"Toxicological Sciences 130(1), 70-81 (2012).
Saag, M.S., (2006), "Emtricitabine, a new antiretroviral agent with activity against HIV and hepatitis B virus", *Clin Infect Dis.*, 42:126-31.
Schenone et al. (1990) "Reaction of 2-Dimethylaminomethylene-1,3-diones with Dinucleophiles. VIII. Synthesis of Ethyl and Methyl 2,4-disubstituted 5-Pyrimidinecarboxylates" 27(2): 295-305.
SciFinder Journal (2013) "Bridged Oxazine Search" CAS Registry 248280-06-0. American Cancer Society: 1-3.
Song, I. et al. (2010) "Lack of Interaction Between the HIV Integrase Inhibitor S/GSK1349572 and Tenofovir in Healthy Subjects" JAIDS 55(3):365-367.
Song, I. et al. (2012) "Effect of Food on the Pharmacokinetics of the Integrase Inhibitor Dolutegravir" Antimicrob Agents and Chemother 56(3):1627-1629.

(56) References Cited

OTHER PUBLICATIONS

Song, I. et al. (2013) "Dolutegrvir Has No Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.

Song, I. et al. (2013) "Pharmacokinetics (PK) and PK.sub.— Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy;Sep. 10-13; Denver, CO.

Soriano, V., et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation; EACS; Oct. 12-15; Belgrade, Serbia.

Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIVPathogenesis, Treatment and Prevention Jun. 30-Jul. 3; Kuala Lumpur, Malaysia.

Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.

Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.

Springthorpe et. al (2007) "From ATP to AZD61640: The Discovery of an Orally Active Reversible P2Y(12) Receptor Antagonist for the Prevention of Thrombosis." Biorganic & Medicinal Chemistry Letters, 17(21):6013-6018.

Stellbrink, H. et al. (2013) "Dolutegravir in antiretroviral-naive adults with HIV-1: 96-week results from a randomized dose-ranging study" AIDS 27:1771-1778.

Summa, V., et al. (2006) "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species" J. Med. Chem; 49:6646-6649.

Summary of Product Characteristics—Annex I, Leaflet, 62 pages—EU—Triumeq [downloaded Sep. 8, 2014].

Tao Y. et al. "Stereoselective synthesis of disubstituted 3(2H)—furanones via catalytic intramolecular C-H insertion reactions of [alpha]-diazo-[beta]-keto esters including asymmetric induction" Tetrahedron Letters, 35(39): 7626-7272.

Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans,LA.

Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.

Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.

Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page; retrieved byHaolun Jin.

Thomson Reuters Drug News "Results from phase III trials of dolutegravir presented," Fri Jul. 5, 2013, 1 page; retrieved by Haolun Jin.

Trinite, B. et al. (2013) "An HIV-1 Replication Pathway Utilizing Reverse Transcription Products That Fail to Integrate" Journal of Virology 87(23):12701-12720.

Tseng, A. et al. (2014) "Drug Interactions with Integrase Inhibitors" Pharm. D.

Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infectious Disease12(2):111-118.

Wai, J., et al.(2007) "Dihydroxypyridopyrazine-1,6-dione HIV-1 Integrase Inhibitors" Bioorganic & Medicinal Chemistry Letters; 17:5595-5599.

Walmsley, S. et al. (2012) "Dolutegravir (DTG; S/GSK1349572) + Abacavir/Lamivudine Once Daily Statistically Superior to Tenofovir/Emtricitabine/Efavirenz: 48-Week Results—SINGLE (ING114467)" Presentation H-556b; 52nd Interscience Conference onAntimicrobial Agents and Chemotherapy; Sep. 9-12; San Francisco, CA.

Walmsley, S. et al. (2013) "Dolutegravir plus Abacavir-Lamivudine for the Treatment of HIV-1 Infection" N Engl J Med 369(19):1807-1818.

Wang, F. et al. (1999) "Modifications of norditerpenoid alkaloids. I. N-deethylation reactions" Abstract, Chinese Chemical Letters 10(5):375-378.

Wang, F. et al. (2005) "To seek an approach toward the chemical conversion of C19-diterpenoid alkaloids to taxoids" Tetrahedron 61(8):2149-2167.

Wang, H. et al. (2015) "An Efficient and Highly Diastereoselective Synthesis of GSK1265744, a Potent HIV Integrase Inhibitor" Org. Letters 17:564-567.

Wang, Y., et al., (2002) "Switch in asymmetric induction sense in cycloadditions using camphor-based nitroso dienop", Tetrahedron: Asymmetry 13:691-5.

Weller, S. et al. (2013) "Pharmacokinetics (PK) and Safety of Dolutegravir (DTG) in Subjects With Severe Renal Impairment and Healthy Controls" Poster A-1571; 53rd Interscience Conference on Antimicrobial Agents and Chemotherapy; Sep. 10-13; Denver,CO.

Weller, S., et al., "Bioequivalence of a Dolutegravir, Abacavir, and Lamivudine Fixed-Dose Combination Tablet and the Effect of Food," 53rd Interscience Conference on Antimicrobial Agents and Chemotherapy; Sep. 10-13, 2013, Denver, CO, 1 page.

Weller, S., et al., (2014) "Bioequivalence of a Dolutegravir, Abacavir, and Lamivudine Fixed-Dose Combination Tablet and the Effect of Food," Clinical Science: Acquired Immune Deficiency Syndrome 66(4): 393-398.

Wensing, A. et al. (2014) "Special Contribution 2014 Update of the Drug Resistance Mutations in HIV-1" IAS-USA Topics in Antiviral Medicine 22(3):642-650.

Wolkowicz, U. et al. (2014) "Structural Basis of Mos1 Transposase Inhibition by the Anti-retroviral Drug Raltegravir" ACS Chem. Biol. 9:743-751.

Wu Y.Q. et al. (1993) "Preparation of the pure diastereomeric forms of S-(5'-deoxy-5'-adenosyl)-1-ammonio-4-methyl sulfonio-2 cyclopentene and their evaluation as irreversible inhibitors of S-adenosylmethionine decarboxylase from *Escherichia coli*" Bioorganic & Medicinal Chemistry, 1(5)349-360.

Wu, B. et al. (2009) "Enantioselective Desymmetrization of meso-Aziridines with TMSN.sub.3 or TMSCN Catalyzed by Discrete Yttrium Complexes" Supporting Information. Ohio State University: Dept. of Chemistry. 64 pages.

Wu, B. et al. (2009) "Enantioselective Desymmetrization of meso-Aziridines with TMSN.sub.3 or TMSCN Catalyzed by Discrete Yttrium Complexes" Supporting Material Angew. Chem. Int. Ed. 48:1126-1129.

Yoshifumi et al. (2015) "Dioxanone-Fused Dienes Enable Highly Endo-Selective Intramolecular Diels-Alder Reactions" Organic Letters, 17(11): 2756-2759; 2758: Scheme 7, compounds 10a and 10b.

Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.

Zheng, X. et al. (2008) "Rapid analysis of a Chinese herbal prescription by liquid chromatography-time-of-flight tandem mass spectrometry" Abstract, Journal of Chromatography A 1206(2:140-146).

(56) References Cited

OTHER PUBLICATIONS

Caira M., (1998) "Crystalline Polymorphism of Organic Compounds." Dept of Chemistry: Topics in Current Chemistry vol. 198: pp. 164-208.
International Search Report—Written Opinion dated Sep. 29, 2015 for PCT/US2015/036784.
Office Action dated Jan. 30, 2018 in JP 2016-574182, 5pgs.
Office Action dated Aug. 30, 2017 for BO App. No. SP125-2015, 10pgs.
IPRP and Written Opinion dated Dec. 29, 2016 for PCT/US2015/036757.
Publication and International Search Report dated Dec. 23, 2015 for PCT/US2015/036757.

* cited by examiner

CRYSTALLINE FORMS OF (2R,5S,13AR)-8-HYDROXY-7,9-DIOXO-N-(2,4,6-TRIFLUORO-BENZYL)-2,3,4,5,7,9,13,13A-OCTAHYDRO-2,5-METHANOPYRIDO[1',2':4,5]PYRAZINO[2,1-B] [1,3] OXAZEPINE-10-CARBOXAMIDE

CROSS REFERENCE TO RELATED APPLICATIONS

This Application is a Divisional of application Ser. No. 14/745,121 filed on Jun. 19, 2015, application Ser. No. 14/745,121 claims the benefit of U.S. Provisional Application 62/017,183 filed on Jun. 25, 2014 and U.S. Provisional Application 62/015,238 filed on Jun. 20, 2014. The entire contents of these applications are incorporated herein by reference in their entirety.

FIELD

The present invention relates to novel crystalline forms and co-crystals of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, the pharmaceutical formulations, and the therapeutic uses thereof.

BACKGROUND

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. N. Engl. J Med. (1998) 338:853-860; Richman, D. D. Nature (2001) 410:995-1001).

A goal of antiretroviral therapy is to achieve viral suppression in the HIV infected patient. Treatment guidelines published by the United States Department of Health and Human Services provide that achievement of viral suppression requires the use of combination therapies, i.e., several drugs from at least two or more drug classes. In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

As discussed in co-pending U.S. application Ser. No. 14/133,855, filed Dec. 19, 2013 entitled "POLYCYCLIC-CARBAMOYLPYRIDONE COMPOUNDS AND THEIR PHARMACEUTICAL USE", (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide demonstrates anti-viral activity. As discussed in co-pending application PCT Serial No. US2013/076367, filed Dec. 19, 2013 entitled "POLYCYCLIC-CARBAMOYLPYRIDONE COMPOUNDS AND THEIR PHARMACEUTICAL USE", (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide demonstrates anti-viral activity.

(2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, (Formula I), has the following structure:

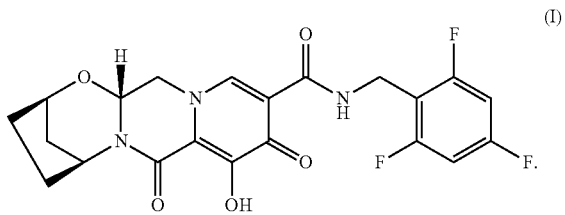 [SMILES: O=C(NCc1c(F)cc(F)cc1F)c1cn2c(c(O)c1=O)C(=O)N1[C@H]3CC[C@H](C3)O[C@@H]1C2]

It is desired to have physically stable forms of the compound that are suitable for the therapeutic use and the manufacturing process.

SUMMARY

In one aspect, the present invention is directed to novel forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In one embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I.

In a further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form II.

In a still further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.

In a yet further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form IV.

In a yet further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form V.

In a yet further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form VI.

In a yet further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form VII.

In a yet further embodiment, the present invention is directed to (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form VIII.

In a certain embodiment, the present invention is directed to a fumaric acid co-crystal of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In another embodiment, the present invention is directed to a citric acid co-crystal of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In yet another embodiment, the present invention is directed to an oxalic acid co-crystal of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In particular embodiments, the present invention is directed to crystalline forms and co-crystals of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In a further aspect, the present invention is directed to novel forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula II):

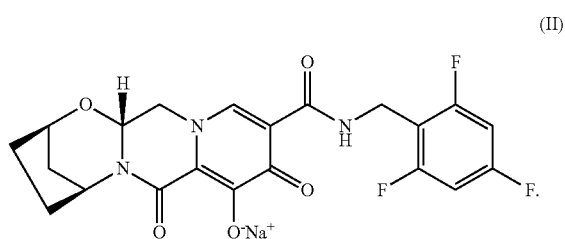

(II)

In a still further embodiment, the present invention is directed to sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In yet a further aspect, the present invention is directed to novel forms of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula III):

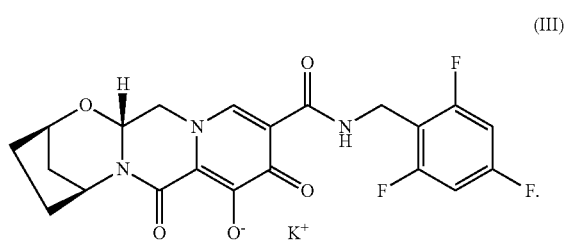 [SMILES: O=C(NCc1c(F)cc(F)cc1F)c1cn2c(c([O-])c1=O)C(=O)N1[C@H]3CC[C@H](C3)O[C@@H]1C2 ; [K+]]

(III)

In yet another embodiment, the present invention is directed to potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In yet another embodiment, the present invention is directed to potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form II.

In yet another embodiment, the present invention is directed to potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form III.

In a still other embodiment, the present invention is directed to hydrated potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In still another embodiment, the present invention is directed to methods of treating or prophylactically preventing an HIV infection by administering a compound (e.g. Formulas (I), (II), and/or (III)) provided herein.

In still another embodiment, the present invention is directed to a compound (e.g. Formulas (I), (II), and/or (III)) provided herein for use in methods of treating or prophylactically preventing an HIV infection.

In still another embodiment, the present invention is directed to the use of a compound (e.g. Formulas (I), (II), and/or (III)) provided herein in the manufacture of a medicament for treating or prophylactically preventing HIV infection.

DETAILED DESCRIPTION

Figure 1:
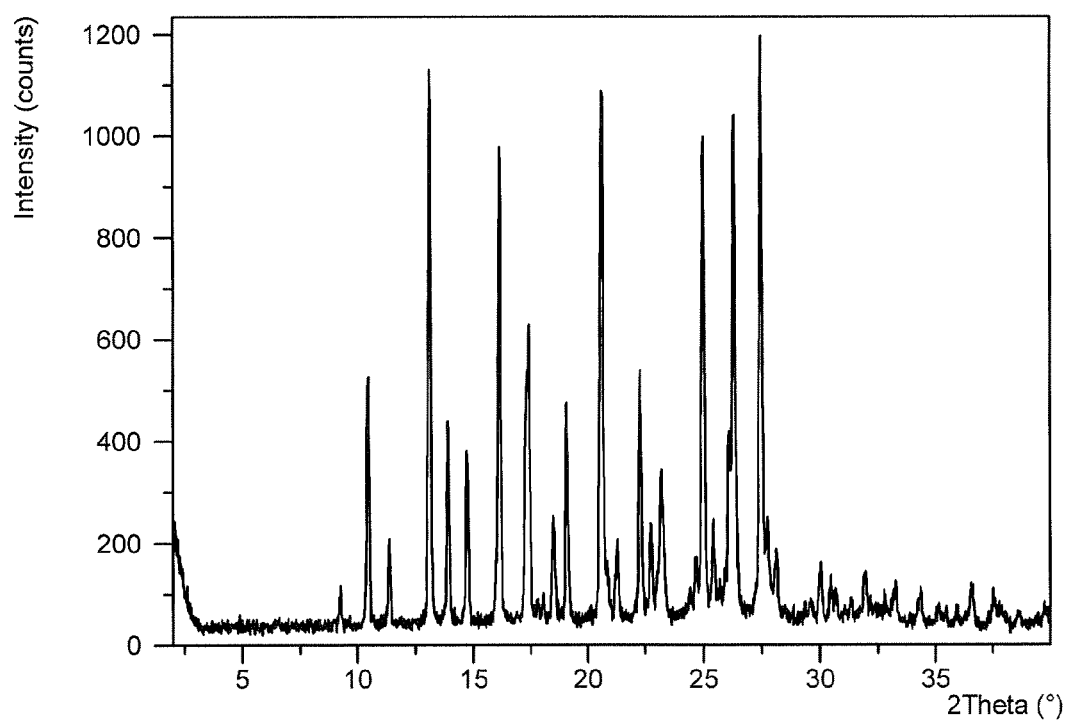
FIG. 1: XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I.

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a compound" or "e.g. Formulas (I), (II), and/or (III)" includes the polymorphic, salt, co-crystal, and solvate forms of the formulas and/or compounds disclosed herein. Thus, the appearances or the phrases "a compound" or "e.g. Formulas (I), (II), and/or (III)" includes Forms I-VIII of Formula I, Form I of Formula II, Forms I-II of Formula III, and/or the fumaric acid, citric acid, and oxalic acid co-crystals as described herein.

The invention disclosed herein is also meant to encompass all pharmaceutically acceptable compounds of Formulas (I), (II), and (III) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formulas (I), (II) and (III), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formulas (I), (II), (III) can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

In certain embodiments, the term "treatment" is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life. In certain embodiments, the term "treatment" as used herein is intended to mean the administration of a compound or composition according to the present invention to alleviate or eliminate symptoms of HIV infection and/or to reduce viral load in a patient. In certain embodiments, the term "treatment" as used herein is further or alternatively intended to mean the administration of a compound or composition according to the present invention to maintain a reduced viral load in a patient. The term "treatment" also encompasses the administration of a compound or composition according to the present invention post-exposure of the individual to the virus but before the appearance of symptoms of the disease; and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life. In certain embodiments, the term "treatment" as used herein is further or alternatively intended to mean the administration of a compound or composition according to the present invention post-exposure of the individual to the virus as a subsequent or additional therapy to a first-line therapy (e.g., for maintenance of low viral load).

"Prevention" or "preventing" means any treatment of a disease or condition that causes the clinical symptoms of the disease or condition not to develop. The term "prevention" also encompasses the administration of a compound or composition according to the present invention pre-exposure of the individual to the virus (e.g., pre-exposure prophylaxis), to prevent the appearance of symptoms of the disease and/or to prevent the virus from reaching detectible levels in the blood.

The terms "Subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In one embodiment, the subject (or the patient) is a human. "Human (or patient) in need thereof" refers to a human who may have or is suspect to have diseases or conditions that would benefit from certain treatment; for example, being treated with the compounds disclosed herein according to the present application.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

A "tautomer" refers to a proton shift from one atom of a molecule to another atom of the same molecule. The present invention includes tautomers of any said compounds.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical carrier.

Crystalline Forms

Formula I

It is desirable to develop a crystalline form of (2R,5S, 13aR)-8-hydroxy-7,9-dioxo-N-(2,4,6-trifluorobenzyl)-2,3, 4,5,7,9,13,13a-octahydro-2,5-methanopyrido[1',2':4,5] pyrazino[2,1-b][1,3]oxazepine-10-carboxamide that may be useful in the synthesis of (2R,5S,13aR)-8-hydroxy-7,9-di-oxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. A form of a (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide may be an intermediate to the synthesis of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. A polymorphic form or polymorph or cocrystal may have properties such as bioavailability and stability at certain conditions that may be suitable for medical or pharmaceutical uses.

A crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide may provide advantages such as: improving the manufacturing process of an active agent or the stability or storability of a drug product form of the compound or an active ingredient, and/or having suitable bioavailability and/or stability as an active agent.

The use of certain solvents has been found to produce different polymorphic forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, including any one or more of polymorphic Forms I, II, III, IV, V, VI, VII, and VIII, which may exhibit one or more favorable characteristics described above. The processes for the preparation of the polymorphs described herein, and characterization of these polymorphs are described in greater detail below.

The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may also be named or identified as (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide under IUPAC and 2,5-Methanopyrido[1',2':4,5]pyrazino[2,1-b][1,3]oxazepine-10-carboxamide, 2,3,4,5,7,9,13,13a-octahydro-8-hydroxy-7,9-dioxo-N-[(2,4,6-trifluorophenyl)methyl]-, (2R,5S,13aR)- under CAS; CAS Registry Number 1611493-60-7.

In particular embodiments, crystalline forms and co-crystals of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide are disclosed.

Formula 1, Form I

Figure 7:
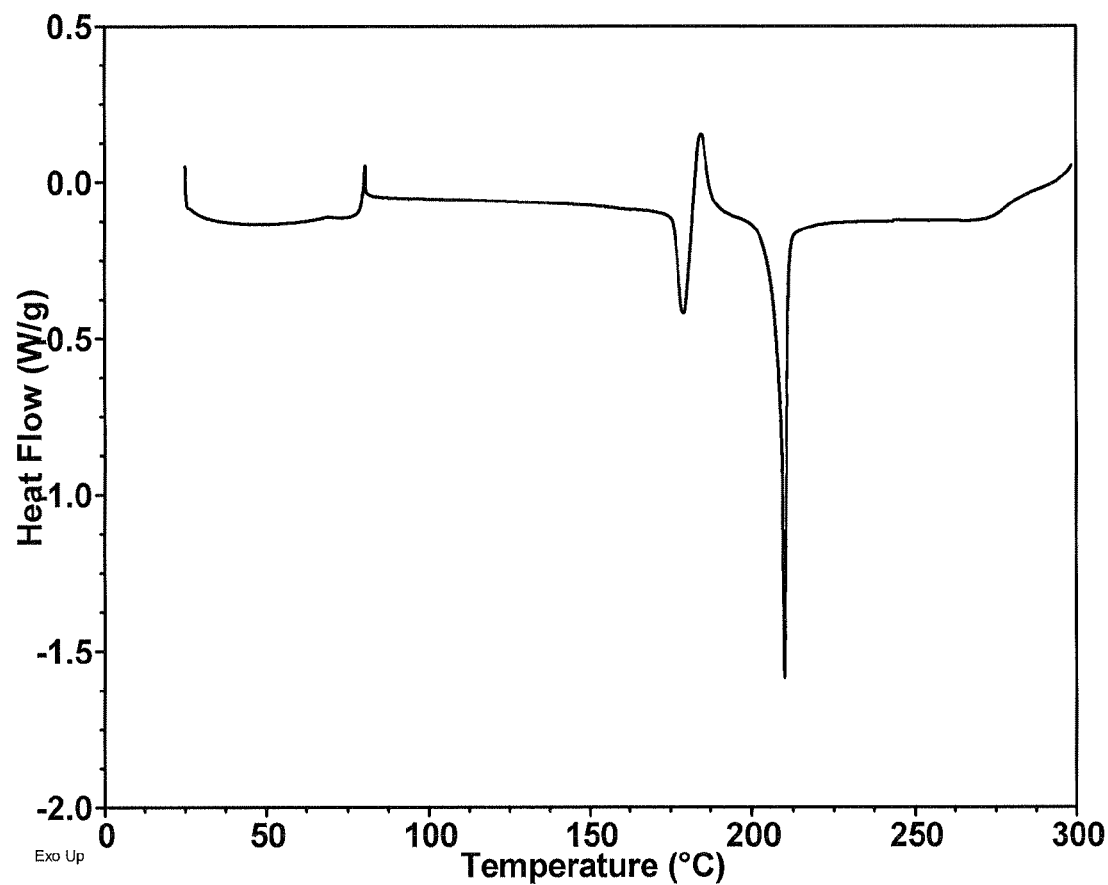
FIG. 7: DSC for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I.
Figure 10:
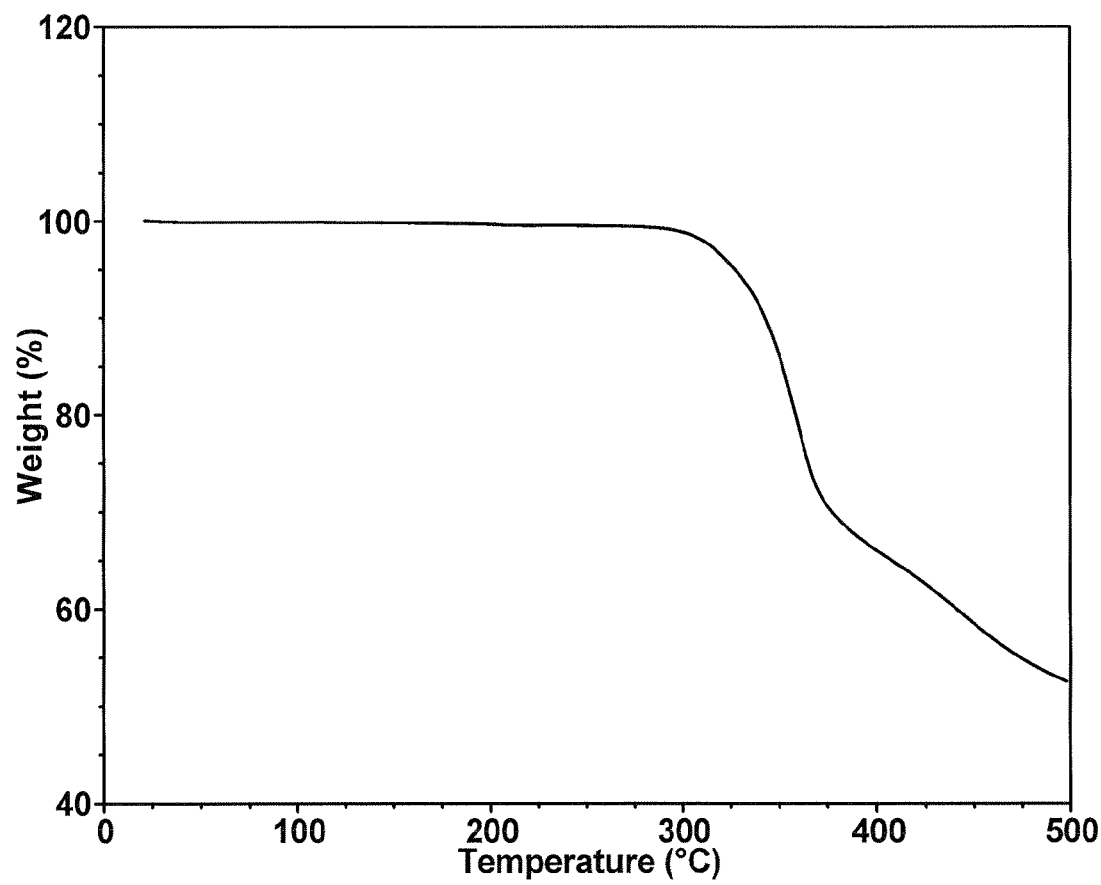
FIG. 10: TGA for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I.
Figure 13:
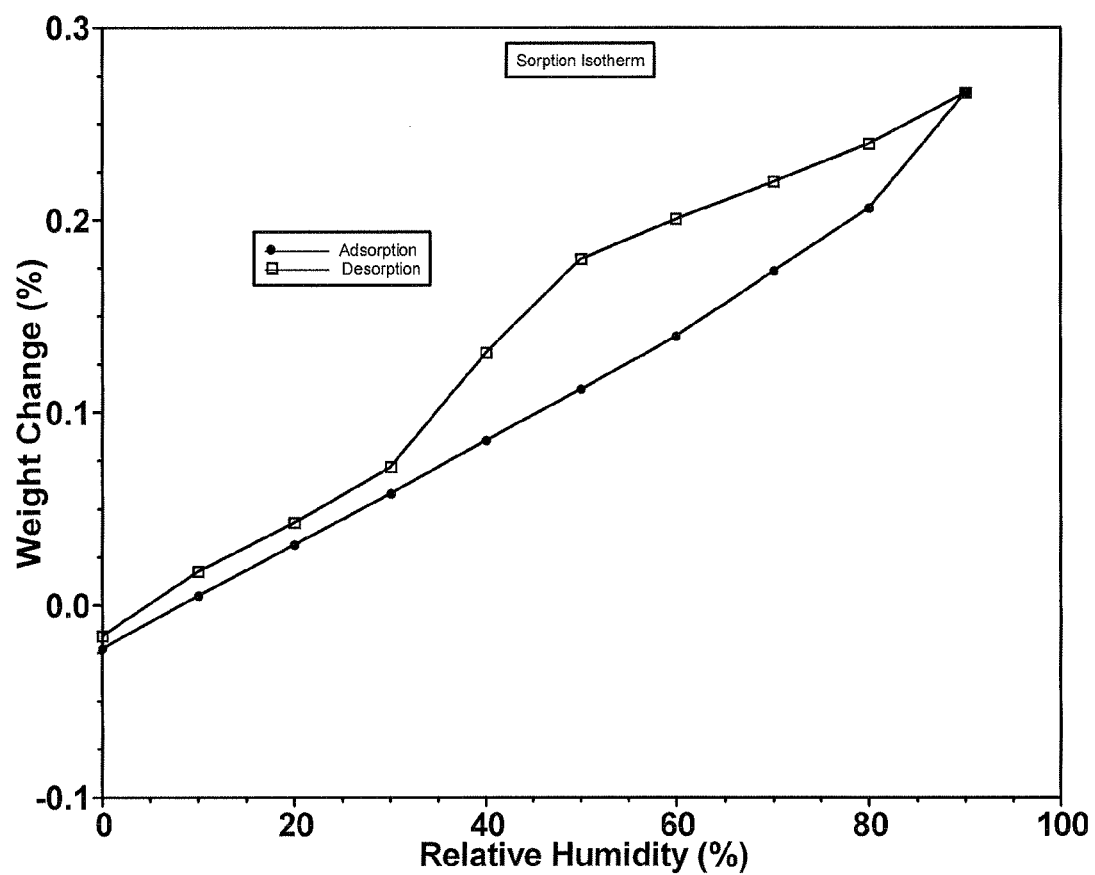
FIG. 13: DVS for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I.

In one embodiment, provided is polymorphic Form I of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the polymorph exhibits an X-ray powder diffraction (XRPD) pattern substantially as shown in FIG. 1. Polymorphic Form I may exhibit a differential scanning calorimetry (DSC) thermogram substantially as shown in FIG. 7. Polymorphic Form I may exhibit a thermographic analysis (TGA) graph substantially as shown in FIG. 10. Polymorphic Form I may exhibit dynamic vapour sorption (DVS) graphs substantially as shown in FIG. 13.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

Polymorphic Form I may have a unit cell as determined by crystal X-ray crystallography of the following dimensions: a=11.4498 (4) Å; b=8.4767 (3) Å; c=19.9163 (8) Å; α=90°; β=106.286 (2)°; and γ=90°.

In some embodiments of polymorphic Form I, at least one, at least two, at least three, at least four, at least five, at least six, at least seven, at least eight, at least nine, at least ten, or all of the following (a)-(k) apply: (a) polymorphic Form I has an XRPD pattern substantially as shown in FIG. 1; (b) polymorphic Form I has a DSC thermogram substantially as shown in FIG. 7; (c) polymorphic Form I has a TGA graph substantially as shown in FIG. 10; (d) polymorphic Form I has DVS graphs substantially as shown in FIG. 13; (e) polymorphic Form I has a unit cell, as determined by crystal X-ray crystallography, of the following dimensions: a=11.4498 (4) Å; b=8.4767 (3) Å; c=19.9163 (8) Å; α=90°; β=106.286 (2)°; and γ=90°; (f) polymorphic Form I has an endothermic event onset; (g) polymorphic Form I has a monoclinic crystal system; (h) polymorphic Form I has a P2(1) space group; (i) polymorphic Form I has a volume of 1855.44(12) Å$^3$; (j) polymorphic Form I has a Z value of 4; and (k) polymorphic Form I has a density of 1.609 g/cm$^3$.

In some embodiments, polymorphic Form I has at least one, at least two, at least three, or all of the following properties:
  (a) an XRPD pattern substantially as shown in FIG. 1;
  (b) a DSC thermogram substantially as shown in FIG. 7;
  (c) DVS graphs substantially as shown in FIG. 13; and
  (d) a unit cell, as determined by crystal X-ray crystallography, of the following dimensions: a=11.4498 (4) Å; b=8.4767 (3) Å; c=19.9163 (8) Å; α=90°; β=106.286 (2)°; and γ=90°.

In some embodiments, polymorphic Form I has an XRPD pattern displaying at least two, at least three, at least four, at least five, or at least six of the degree 2θ-reflections with the greatest intensity as the XRPD pattern substantially as shown in FIG. 1.

In certain embodiments, polymorphic Form I has an XRPD pattern comprising degree 2θ-reflections (+/−0.2 degrees 2θ) at 27.4, 13.1, and 17.4. In one embodiment, polymorphic Form I has an XRPD pattern comprising degree 2θ-reflections (+/−0.2 degrees 2θ) at 27.4, 13.1, and 17.4 and one or more of the degree 2θ-reflections (+/−0.2 degrees 2θ) at 10.5, 20.6, and 25.0. In one embodiment, polymorphic Form I has an XRPD pattern comprising degree 2θ-reflections (+/−0.2 degrees 2θ) at 27.4, 13.1, and 17.4 and one of the degree 2θ-reflections (+/−0.2 degrees 2θ) at 10.5, 20.6, and 25.0. In one embodiment, polymorphic Form I has an XRPD pattern comprising degree 2θ-reflections (+/−0.2 degrees 2θ) at 27.4, 13.1, and 17.4 and two of the degree 2θ-reflections (+/−0.2 degrees 2θ) at 10.5, 20.6, and 25.0. In one embodiment, polymorphic Form I has an XRPD pattern comprising degree 2θ-reflections (+/−0.2 degrees 2θ) at 27.4, 13.1, and 17.4 and three of the degree 2θ-reflections (+/−0.2 degrees 2θ) at 10.5, 20.6, and 25.0. In one embodiment, polymorphic Form I has an XRPD pattern comprising degree 2θ-reflections (+/−0.2 degrees 2θ) at 27.4, 13.1, 17.4, 10.5, 20.6, and 25.0. In one embodiment, polymorphic Form I has an XRPD pattern comprising degree 2θ-reflections (+/−0.2 degrees 2θ) at 27.4, 13.1, 17.4, 10.5, 20.6, 25.0, 16.2, and 22.3. In one embodiment, polymorphic Form I has an XRPD pattern comprising any three degree 2θ-reflections (+/−0.2 degrees 2θ) selected from the group consisting of 27.4, 13.1, 17.4, 10.5, 20.6, 25.0, 16.2, 22.3, 13.9, 11.4, and 9.3.

Formula 1, Form II

Figure 2:
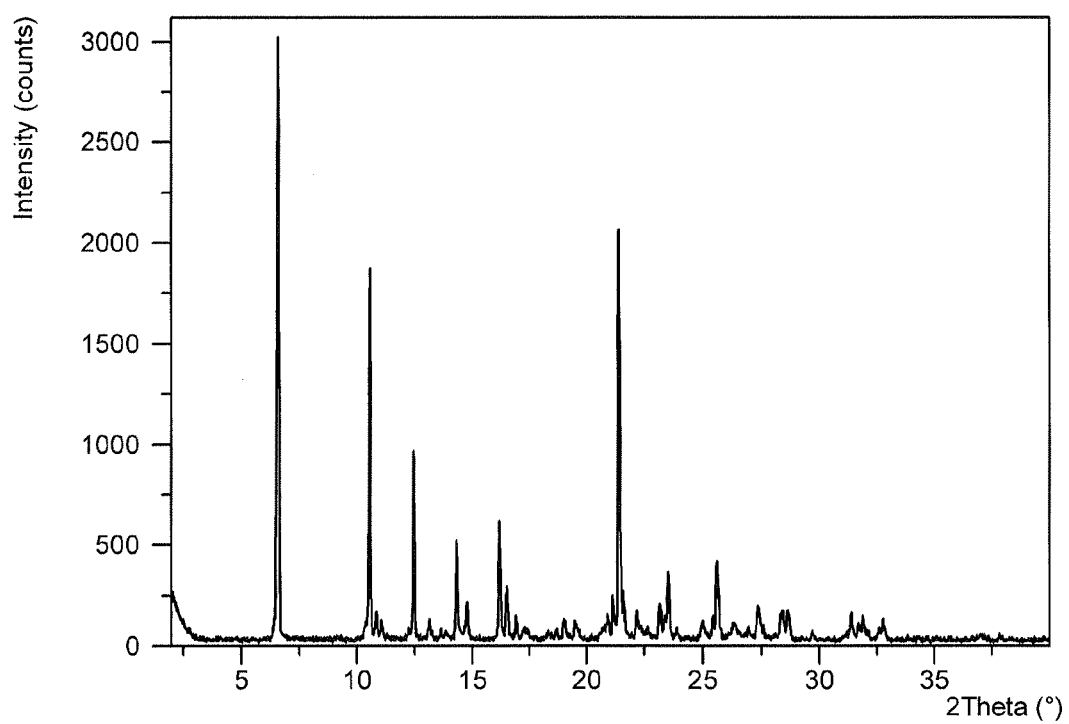
FIG. 2: XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form II.

In one embodiment, provided is polymorphic Form II of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the polymorph exhibits an X-ray powder diffraction (XRPD) pattern substantially as shown in FIG. 2.

Polymorphic Form II may have a unit cell as determined by crystal X-ray crystallography of the following dimensions: a=8.5226 (7) Å; b=26.934 (2) Å; c=8.6861 (8) Å; α=90°; β=101.862 (2)°; and γ=90°.

In some embodiments of polymorphic Form II, at least one, at least two, at least three, at least four, at least five, at least six, or all of the following (a)-(g) apply: (a) polymorphic Form II has an XRPD pattern substantially as shown in FIG. 2; (b) polymorphic Form II has a unit cell, as determined by crystal X-ray crystallography, of the following dimensions: a=8.5226 (7) Å; b=26.934 (2) Å; c=8.6861 (8) Å; α=90°; β=101.862 (2)°; and γ=90°; (c) polymorphic Form II has a monoclinic crystal system; (d) polymorphic Form II has a P2(1) space group; (e) polymorphic Form II has a volume of 1951.3(3) Å$^3$; (f) polymorphic Form II has a Z value of 4; and (g) polymorphic Form II has a density of 1.537 Mg/m$^3$.

In some embodiments, polymorphic Form II has at least one, or all of the following properties:
(a) an XRPD pattern substantially as shown in FIG. 2;
(b) a unit cell, as determined by crystal X-ray crystallography, of the following dimensions: a=8.5226 (7) Å; b=26.934 (2) Å; c=8.6861 (8) Å; α=90°; β=101.862 (2)°; and γ=90°.

In some embodiments, polymorphic Form II has an XRPD pattern displaying at least two, at least three, at least four, at least five, or at least six of the degree 2θ-reflections with the greatest intensity as the XRPD pattern substantially as shown in FIG. 2.

In certain embodiments, polymorphic Form II has an XRPD pattern comprising degree 2θ-reflections (+/−0.2 degrees 2θ) at 6.6, 21.4, and 10.6. In one embodiment, polymorphic Form II has an XRPD pattern comprising degree 2θ-reflections (+/−0.2 degrees 2θ) at 6.6, 21.4, and 10.6 and one or more of the degree 2θ-reflections (+/−0.2 degrees 2θ) at 12.5, 16.2, and 14.3. In one embodiment, polymorphic Form II has an XRPD pattern comprising degree 2θ-reflections (+/−0.2 degrees 2θ) at 6.6, 21.4, and 10.6 and one of the degree 2θ-reflections (+/−0.2 degrees 2θ) at 12.5, 16.2, and 14.3. In one embodiment, polymorphic Form II has an XRPD pattern comprising degree 2θ-reflections (+/−0.2 degrees 2θ) at 6.6, 21.4, and 10.6 and two of the degree 2θ-reflections (+/−0.2 degrees 2θ) at 12.5, 16.2, and 14.3. In one embodiment, polymorphic Form II has an XRPD pattern comprising degree 2θ-reflections (+/−0.2 degrees 2θ) at 6.6, 21.4, and 10.6 and three of the degree 2θ-reflections (+/−0.2 degrees 2θ) at 12.5, 16.2, and 14.3. In one embodiment, polymorphic Form II has an XRPD pattern comprising degree 2θ-reflections (+/−0.2 degrees 2θ) at 6.6, 21.4, 10.6, 12.5, 16.2, and 14.3. In one embodiment, polymorphic Form II has an XRPD pattern comprising degree 2θ-reflections (+/−0.2 degrees 2θ) at 6.6, 21.4, 10.6, 12.5, 16.2, 14.3, 25.6, and 23.5. In one embodiment, polymorphic Form II has an XRPD pattern comprising any three degree 2θ-reflections (+/−0.2 degrees 2θ) selected from the group consisting of 6.6, 21.4, 10.6, 12.5, 16.2, 14.3, 25.6, and 23.5.

Formula 1, Form III

Figure 3:
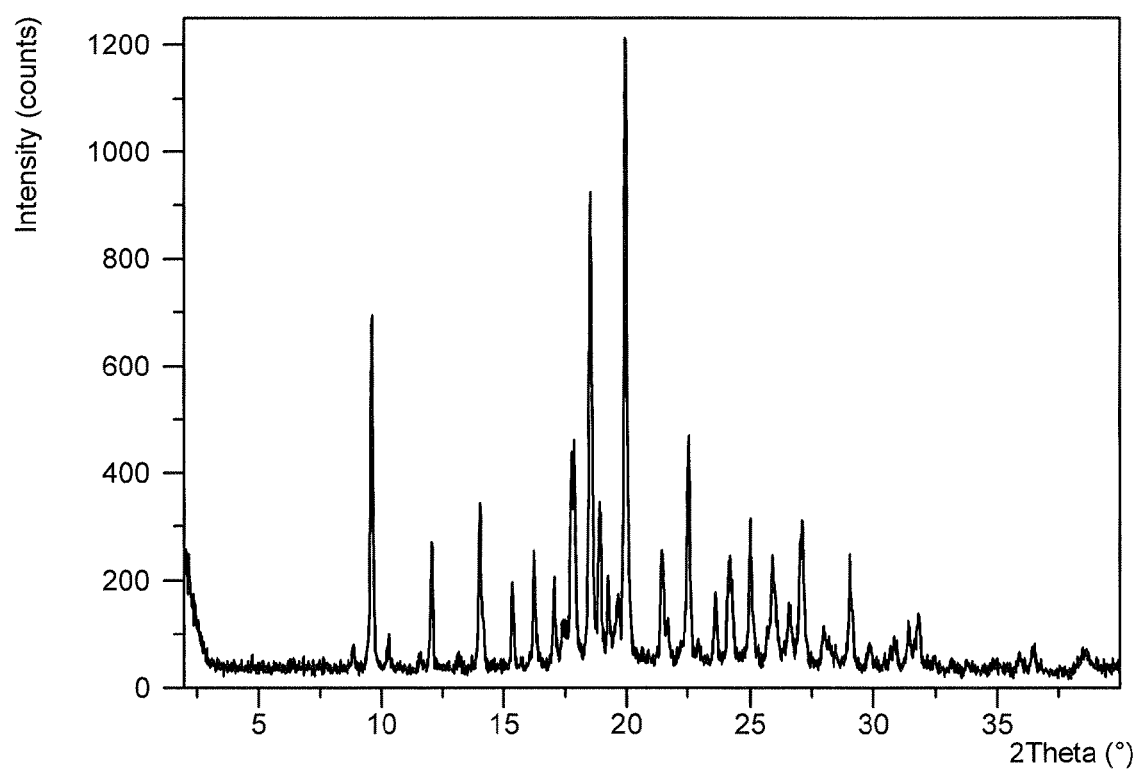
FIG. 3: XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.
Figure 8:
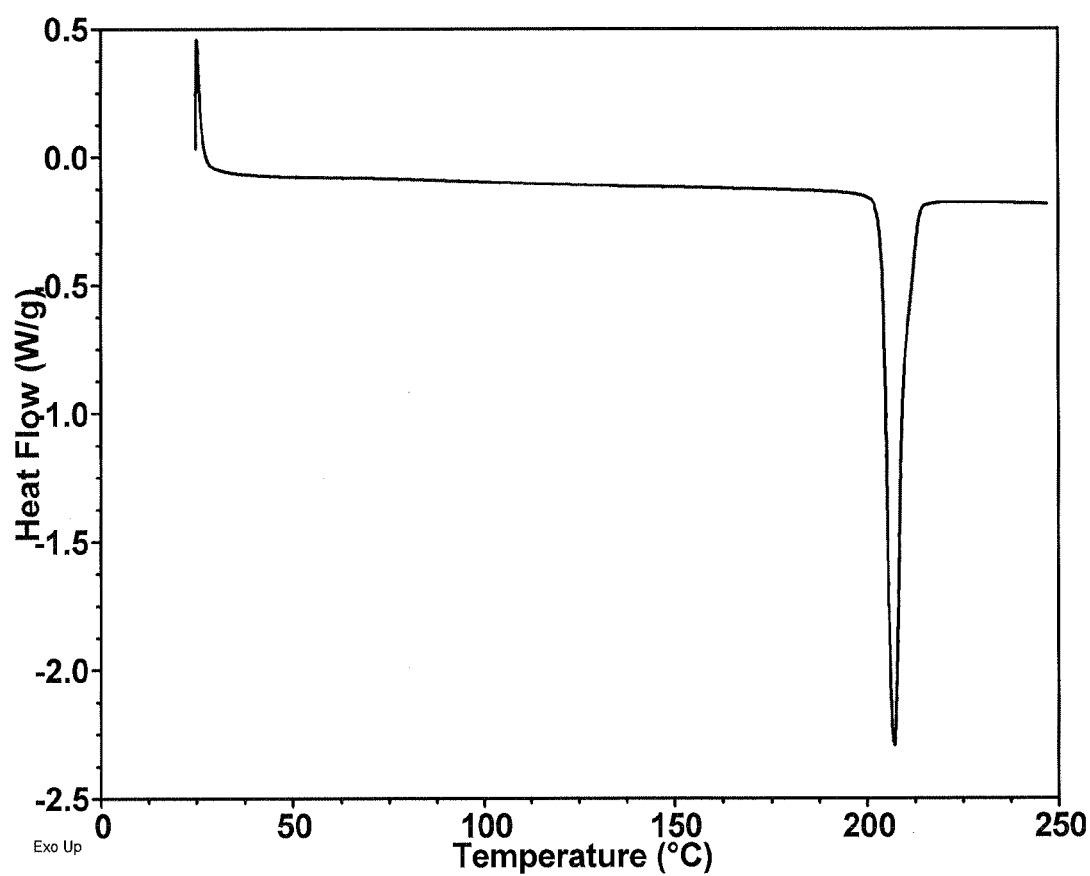
FIG. 8: DSC for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.
Figure 11:
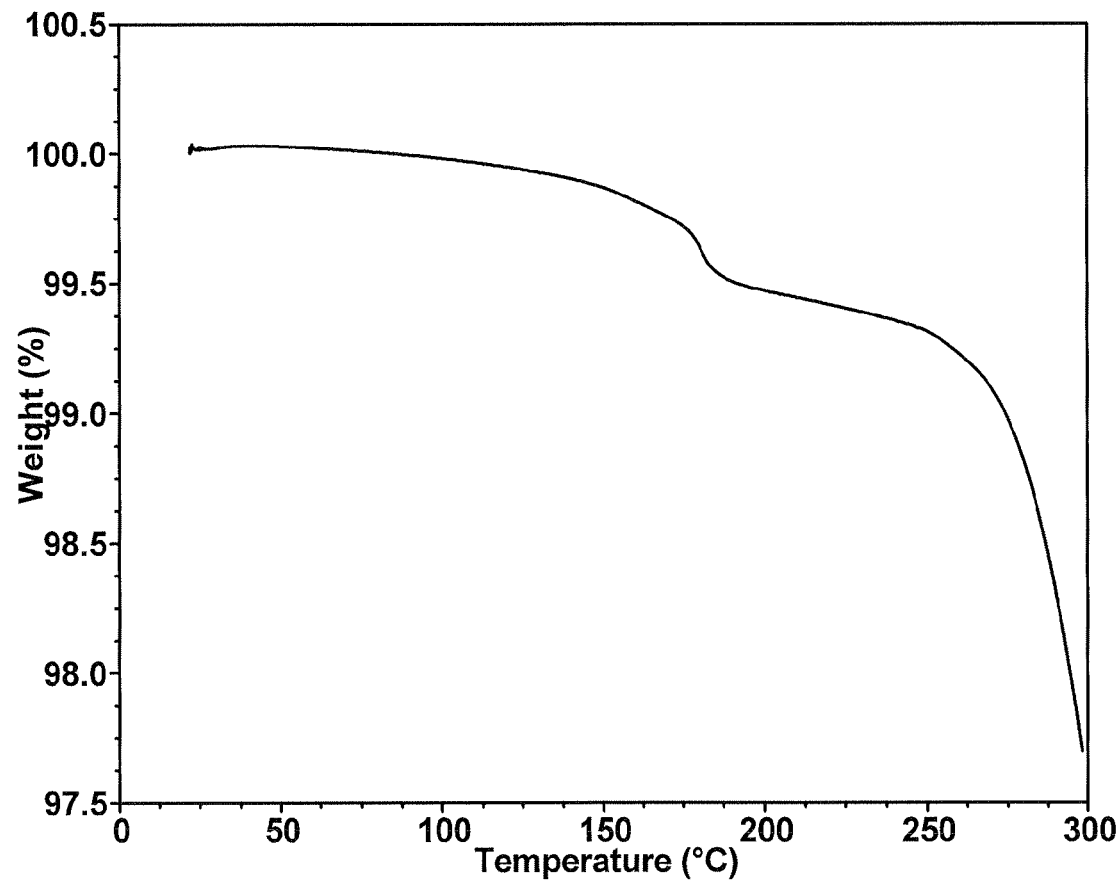
FIG. 11: TGA for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.
Figure 14:
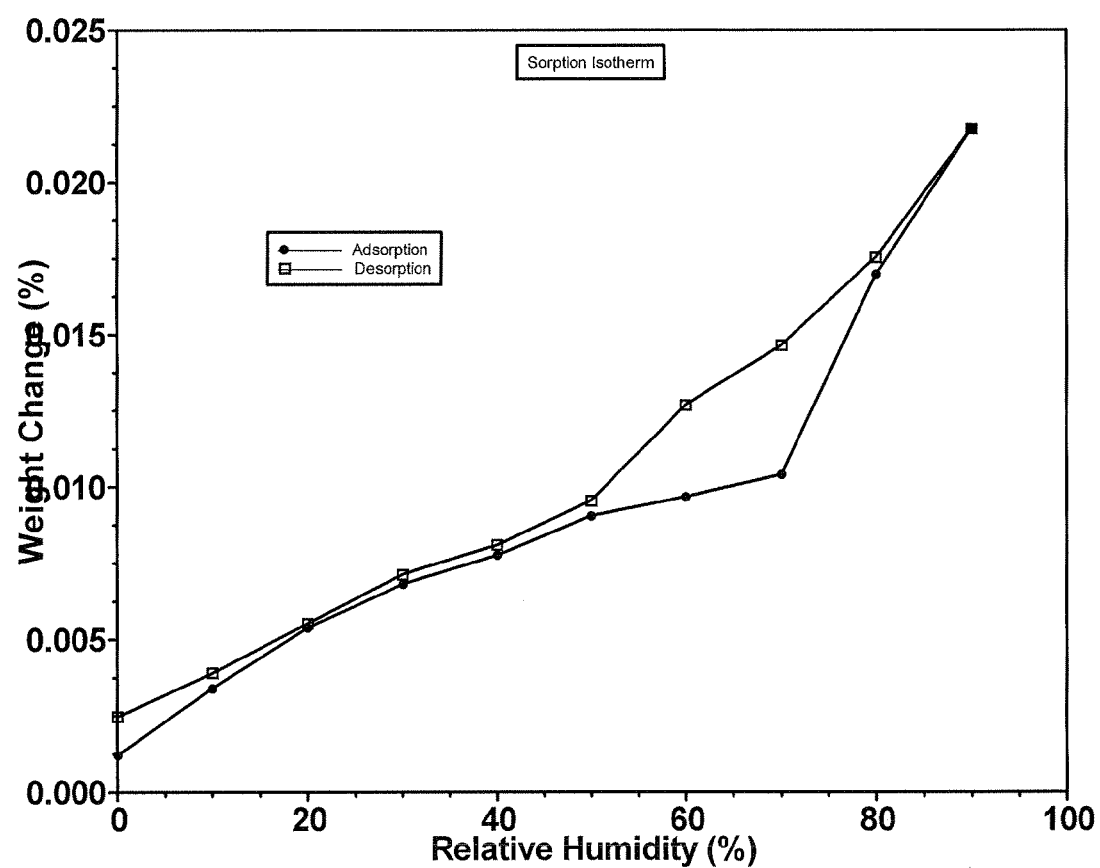
FIG. 14: DVS for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.

In one embodiment, provided is polymorphic Form II of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the polymorph exhibits an X-ray powder diffraction (XRPD) pattern substantially as shown in FIG. 3. Polymorphic Form III may exhibit a differential scanning calorimetry (DSC) thermogram substantially as shown in FIG. 8. Polymorphic Form III may exhibit a thermographic analysis (TGA) graph substantially as shown in FIG. 11. Polymorphic Form III may exhibit dynamic vapour sorption (DVS) graphs substantially as shown in FIG. 14.

Polymorphic Form III may have a unit cell as determined by crystal X-ray crystallography of the following dimensions: a=18.002 (2) Å; b=10.9514 (12) Å; c=20.687 (2) Å; α=90°; β=107.770 (4)°; and γ=90°.

In some embodiments of polymorphic Form III, at least one, at least two, at least three, at least four, at least five, at least six, at least seven, at least eight, at least nine, at least ten, or all of the following (a)-(k) apply: (a) polymorphic Form III has an XRPD pattern substantially as shown in FIG. 3; (b) polymorphic Form III has a DSC thermogram substantially as shown in FIG. 8; (c) polymorphic Form III has a TGA graph substantially as shown in FIG. 11; (d) polymorphic Form III has DVS graphs substantially as shown in FIG. 14; (e) polymorphic Form III has a unit cell, as determined by crystal X-ray crystallography, of the following dimensions: a=18.002 (2) Å; b=10.9514 (12) Å; c=20.687 (2) Å; α=90°; β=107.770 (4)°; and γ=90°; (f) polymorphic Form I has an endothermic event onset (g) polymorphic Form III has a monoclinic crystal system; (h) polymorphic Form III has a P2(1) space group; (i) polymorphic Form III has a volume of 3884.0(8) Å$^3$; (j) polymorphic Form III has a Z value of 8; and (k) polymorphic Form III has a density of 1.537 g/cm$^3$.

In some embodiments, polymorphic Form III has at least one, at least two, at least three, or all of the following properties:
(a) an XRPD pattern substantially as shown in FIG. 3;
(b) a DSC thermogram substantially as shown in FIG. 8;
(c) DVS graphs substantially as shown in FIG. 14; and
(d) a unit cell, as determined by crystal X-ray crystallography, of the following dimensions a=18.002 (2) Å; b=10.9514 (12) Å; c=20.687 (2) Å; α=90°; β=107.770 (4)°; and γ=90°.

In some embodiments, polymorphic Form III has an XRPD pattern displaying at least two, at least three, at least four, at least five, or at least six of the degree 2θ-reflections with the greatest intensity as the XRPD pattern substantially as shown in FIG. 3.

In certain embodiments, polymorphic Form III has an XRPD pattern comprising degree 2θ-reflections (+/−0.2 degrees 2θ) at 20.0, 18.5, and 9.6. In one embodiment, polymorphic Form III has an XRPD pattern comprising degree 2θ-reflections (+/−0.2 degrees 2θ) at 20.0, 18.5, and 9.6 and one or more of the degree 2θ-reflections (+/−0.2 degrees 2θ) at 22.5, 14.0, and 25.0. In one embodiment, polymorphic Form III has an XRPD pattern comprising degree 2θ-reflections (+/−0.2 degrees 2θ) at 20.0, 18.5, and 9.6 and one of the degree 2θ-reflections (+/−0.2 degrees 2θ) at 22.5, 14.0, and 25.0. In one embodiment, polymorphic Form III has an XRPD pattern comprising degree 2θ-reflections (+/−0.2 degrees 2θ) at 20.0, 18.5, and 9.6 and two of the degree 2θ-reflections (+/−0.2 degrees 2θ) at 22.5, 14.0, and 25.0. In one embodiment, polymorphic Form III has an XRPD pattern comprising degree 2θ-reflections (+/−0.2 degrees 2θ) at 20.0, 18.5, and 9.6 and three of the degree 2θ-reflections (+/−0.2 degrees 2θ) at 22.5, 14.0, and 25.0. In one embodiment, polymorphic Form III has an XRPD pattern comprising degree 2θ-reflections (+/−0.2 degrees 2θ) at 20.0, 18.5, 9.6, 22.5, 14.0, and 25.0. In one embodiment, polymorphic Form III has an XRPD pattern comprising degree 2θ-reflections (+/−0.2 degrees 2θ) at 20.0, 18.5, 9.6, 22.5, 14.0, 25.0, 12.1, and 27.0. In one embodiment, polymorphic Form III has an XRPD pattern comprising any three degree 2θ-reflections (+/−0.2 degrees 2θ) selected from the group consisting of 20.0, 18.5, 9.6, 22.5, 14.0, 25.0, 12.1, 27.0, 16.2, and 29.0.

Formula 1, Form IV

Figure 4:
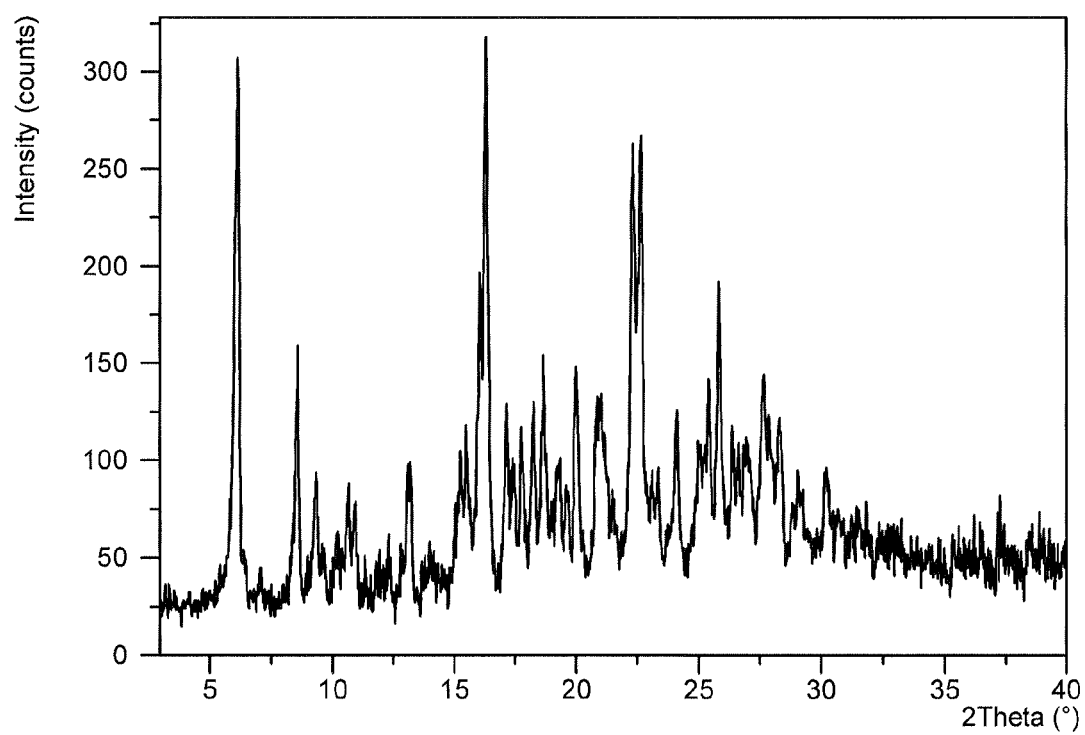
FIG. 4: XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form IV.

In one embodiment, provided is polymorphic Form IV of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the polymorph exhibits an X-ray powder diffraction (XRPD) pattern substantially as shown in FIG. 4.

Polymorphic Form IV may have a unit cell as determined by crystal X-ray crystallography of the following dimensions: a=29.948 (2) Å; b=16.5172 (9) Å; c=13.2051 (8) Å; α=90°; β=108.972 (4)°; and γ=90°.

In some embodiments of polymorphic Form IV, at least one, at least two, at least three, at least four, at least five, at least six, or all of the following (a)-(g) apply: (a) polymorphic Form IV has an XRPD pattern substantially as shown in FIG. 4; (b) polymorphic Form IV has a unit cell, as determined by crystal X-ray crystallography, of the following dimensions: a=29.948 (2) Å; b=16.5172 (9) Å; c=13.2051 (8) Å; α=90°; β=108.972 (4)°; and γ=90°; (c) polymorphic Form IV has a monoclinic crystal system; (d) polymorphic Form IV has a C2 space group; (e) polymorphic Form IV has a volume of 6177.3(7) Å$^3$; (f) polymorphic Form IV has a Z value of 12; and (g) polymorphic Form IV has a density of 1.484 Mg/m$^3$.

In some embodiments, polymorphic Form IV has at least one, or all of the following properties:
 (a) an XRPD pattern substantially as shown in FIG. 4;
 (b) a unit cell, as determined by crystal X-ray crystallography, of the following dimensions: a=29.948 (2) Å; b=16.5172 (9) Å; c=13.2051 (8) Å; α=90°; β=108.972 (4)°; and γ=90°.

In some embodiments, polymorphic Form IV has an XRPD pattern displaying at least two, at least three, at least four, at least five, or at least six of the degree 2θ-reflections with the greatest intensity as the XRPD pattern substantially as shown in FIG. 4.

In certain embodiments, polymorphic Form IV has an XRPD pattern comprising degree 2θ-reflections (+/−0.2 degrees 2θ) at 16.3, 6.2, and 8.6. In one embodiment, polymorphic Form IV has an XRPD pattern comprising degree 2θ-reflections (+/−0.2 degrees 2θ) at 16.3, 6.2, and 8.6 and one or more of the degree 2θ-reflections (+/−0.2 degrees 2θ) at 22.7, 22.3, and 25.8. In one embodiment, polymorphic Form IV has an XRPD pattern comprising degree 2θ-reflections (+/−0.2 degrees 2θ) at 16.3, 6.2, and 8.6 and one of the degree 2θ-reflections (+/−0.2 degrees 2θ) at 22.7, 22.3, and 25.8. In one embodiment, polymorphic Form IV has an XRPD pattern comprising degree 2θ-reflections (+/−0.2 degrees 2θ) at 16.3, 6.2, and 8.6 and two of the degree 2θ-reflections (+/−0.2 degrees 2θ) at 22.7, 22.3, and 25.8. In one embodiment, polymorphic Form IV has an XRPD pattern comprising degree 2θ-reflections (+/−0.2 degrees 2θ) at 16.3, 6.2, and 8.6 and three of the degree 2θ-reflections (+/−0.2 degrees 2θ) at 22.7, 22.3, and 25.8. In one embodiment, polymorphic Form IV has an XRPD pattern comprising degree 2θ-reflections (+/−0.2 degrees 2θ) at 16.3, 6.2, 8.6, 22.7, 22.3, and 25.8. In one embodiment, polymorphic Form IV has an XRPD pattern comprising degree 2θ-reflections (+/−0.2 degrees 2θ) at 16.3, 6.2, 8.6, 22.7, 22.3, 25.8, 20.0, and 18.7. In one embodiment, polymorphic Form IV has an XRPD pattern comprising any three degree 2θ-reflections (+/−0.2 degrees 2θ) selected from the group consisting of 16.3, 6.2, 8.6, 22.7, 22.3, 25.8, 20.0, 18.7, 27.7, and 13.2.

Formula 1, Form V

In one embodiment, provided is polymorphic Form V of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Polymorphic Form V may have a unit cell as determined by crystal X-ray crystallography of the following dimensions: a=8.4993 (6) Å; b=8.7290 (8) Å; c=13.8619 (13) Å; α=99.278 (5)°; β=101.427 (4)°; and γ=100.494 (4)°.

In some embodiments of polymorphic Form V, at least one, at least two, at least three, at least four, at least five, or all of the following (a)-(f) apply: (a) polymorphic Form V has a unit cell, as determined by crystal X-ray crystallography, of the following dimensions: a=8.4993 (6) Å; b=8.7290 (8) Å; c=13.8619 (13) Å; α=99.278 (5)°; β=101.427 (4)°; and γ=100.494 (4)°; (b) polymorphic Form V has a triclinic crystal system; (c) polymorphic Form V has a P2(1) space group; (d) polymorphic Form V has a volume of 970.18(14) Å$^3$; (e) polymorphic Form V has a Z value of 2; and (f) polymorphic Form V has a density of 1.573 Mg/m$^3$.

In some embodiments, polymorphic Form V has the following properties:
 a unit cell, as determined by crystal X-ray crystallography, of the following dimensions: a=8.4993 (6) Å; b=8.7290 (8) Å; c=13.8619 (13) Å; α=99.278 (5)°; β=101.427 (4)°; and γ=100.494 (4)°.

Formula 1, Form VI

In one aspect, provided is polymorphic Form VI of a (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Polymorphic Form VI may have a unit cell as determined by crystal X-ray crystallography of the following dimensions: a=19.5163 (5) Å; b=6.4593 (2) Å; c=16.6066 (5) Å; α=90°; β=103.5680 (13)°; and γ=90°.

In some embodiments of polymorphic Form VI, at least one, at least two, at least three, at least four, at least five, or all of the following (a)-(f) apply: (a) polymorphic Form VI has a unit cell, as determined by crystal X-ray crystallography, of the following dimensions: a=19.5163 (5) Å; b=6.4593 (2) Å; c=16.6066 (5) Å; α=90°; β=103.5680 (13)°; and γ=90°; (b) polymorphic Form VI has a monoclinic crystal system; (c) polymorphic Form V has a P2(1) space group; (d) polymorphic Form VI has a volume of 2035.03 (10) Å$^3$; (e) polymorphic Form V has a Z value of 4; and (f) polymorphic Form V has a density of 1.545 Mg/m$^3$.

In some embodiments, polymorphic Form VI has the following properties:
  (a) a unit cell, as determined by crystal X-ray crystallography, of the following dimensions: a=19.5163 (5) Å; b=6.4593 (2) Å; c=16.6066 (5) Å; α=90°; β=103.5680 (13)°; and γ=90°.

Formula 1, Form VII

In one embodiment, provided is polymorphic Form VII of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Polymorphic Form VII may have a unit cell as determined by crystal X-ray crystallography of the following dimensions: a=30.785 (12) Å; b=16.685 (6) Å; c=25.956 (10) Å; α=90°; β=108.189 (10)°; and γ=90°.

In some embodiments of polymorphic Form VII, at least one, at least two, at least three, at least four, at least five, or all of the following (a)-(f) apply: (a) polymorphic Form VII has a unit cell, as determined by crystal X-ray crystallography, of the following dimensions: a=30.785 (12) Å; b=16.685 (6) Å; c=25.956 (10) Å; α=90°; β=108.189 (10)°; and γ=90°; (b) polymorphic Form VII has a monoclinic crystal system; (c) polymorphic Form VII has a P2(1) space group; (d) polymorphic Form VI has a volume of 12666(8) Å$^3$; (e) polymorphic Form VII has a Z value of 24; and (f) polymorphic Form VII has a density of 1.468 Mg/m$^3$.

In some embodiments, polymorphic Form VI has the following properties:
  (a) a unit cell, as determined by crystal X-ray crystallography, of the following dimensions: a=30.785 (12) Å; b=16.685 (6) Å; c=25.956 (10) Å; α=90°; β=108.189 (10)°; and γ=90°.

Formula 1, Form VIII

In one embodiment, provided is polymorphic Form VIII of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Polymorphic Form VIII may have a unit cell as determined by crystal X-ray crystallography of the following dimensions: a=10.3242 (18) Å; b=10.7826 (17) Å; c=17.848 (3) Å; α=90°; β=105.578 (8)°; and γ=90°.

In some embodiments of polymorphic Form VIII, at least one, at least two, at least three, at least four, at least five, or all of the following (a)-(f) apply: (a) polymorphic Form VIII has a unit cell, as determined by crystal X-ray crystallography, of the following dimensions: a=10.3242 (18) Å; b=10.7826 (17) Å; c=17.848 (3) Å; α=90°; β=105.578 (8)°; and γ=90°; (b) polymorphic Form VIII has a monoclinic crystal system; (c) polymorphic Form VIII has a C2 space group; (d) polymorphic Form VIII has a volume of 1913.9 (6) Å$^3$; (e) polymorphic Form VIII has a Z value of 4; and (f) polymorphic Form VIII has a density of 1.560 Mg/m$^3$.

In some embodiments, polymorphic Form VIII has the following properties:
  (a) a unit cell, as determined by crystal X-ray crystallography, of the following dimensions: a=10.3242 (18) Å; b=10.7826 (17) Å; c=17.848 (3) Å; α=90°; β=105.578 (8)°; and γ=90°.

Formula II

It is desirable to develop a crystalline form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate that may be useful in the synthesis of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may be an intermediate to the synthesis of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may be the final product in the synthesis of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A polymorphic form or polymorph or cocrystal may have properties such as bioavailability and stability at certain conditions that may be suitable for medical or pharmaceutical uses.

A crystalline form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide the advantage of bioavailability and stability, suitable for use as an active ingredient in a pharmaceutical composition. In certain embodiments, a crystalline form sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate provides an advantage of improved bioavailability (Table 3) and/or stability (Table 4). Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide advantages such as: improving the manufacturing process of an active agent or the stability or storability of a drug product form of the compound or an active ingredient, and/or having suitable bioavailability and/or stability as an active agent.

The use of certain solvents has been found to produce different polymorphic forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, including polymorphic Form I, which may exhibit one or more favorable characteristics described above. In certain embodiments, Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate provides an advantage of improved bioavailability (Table 3) and/or stability (Table 4). The processes for the preparation of the polymorphs described herein and characterization of these polymorphs are described in greater detail below.

The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may be named or identified as sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate under IUPAC.

In particular embodiments, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are disclosed.

Formula II, Form I

In a certain embodiment, novel forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula II) are disclosed:

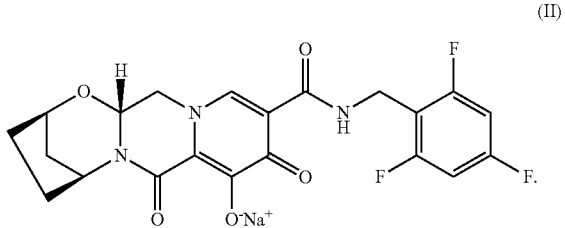

(II)

In a further embodiment, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are disclosed.

In a certain embodiment, sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is disclosed.

Figure 5:
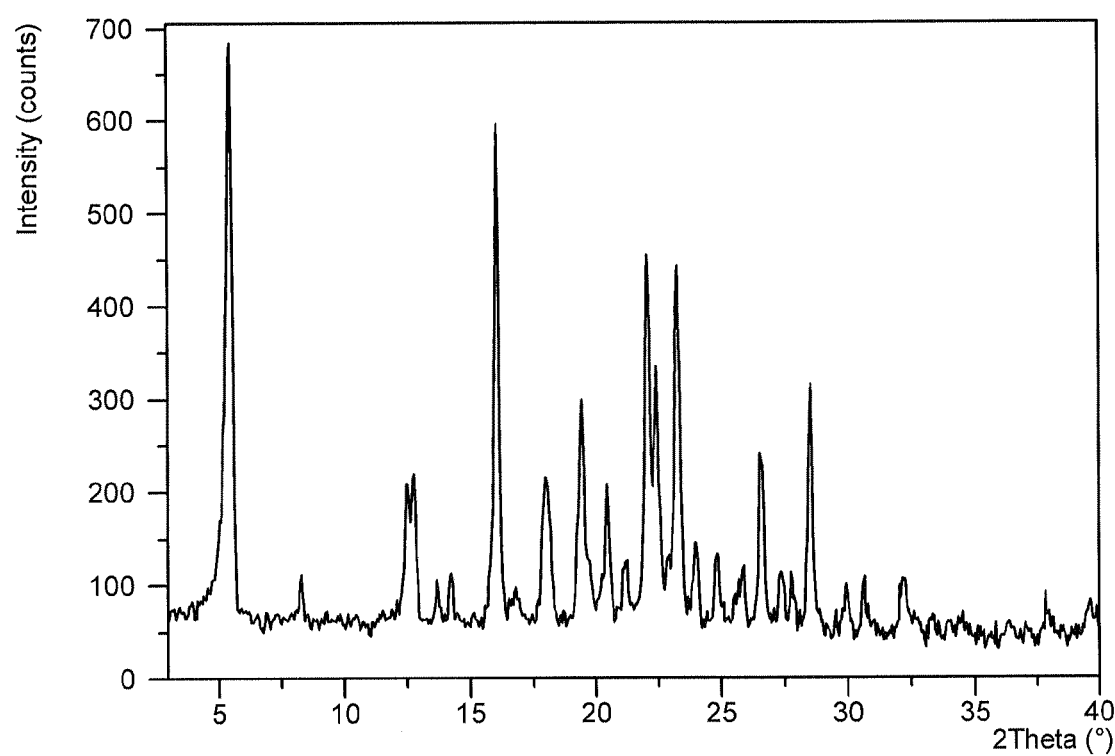
FIG. 5: XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 9:
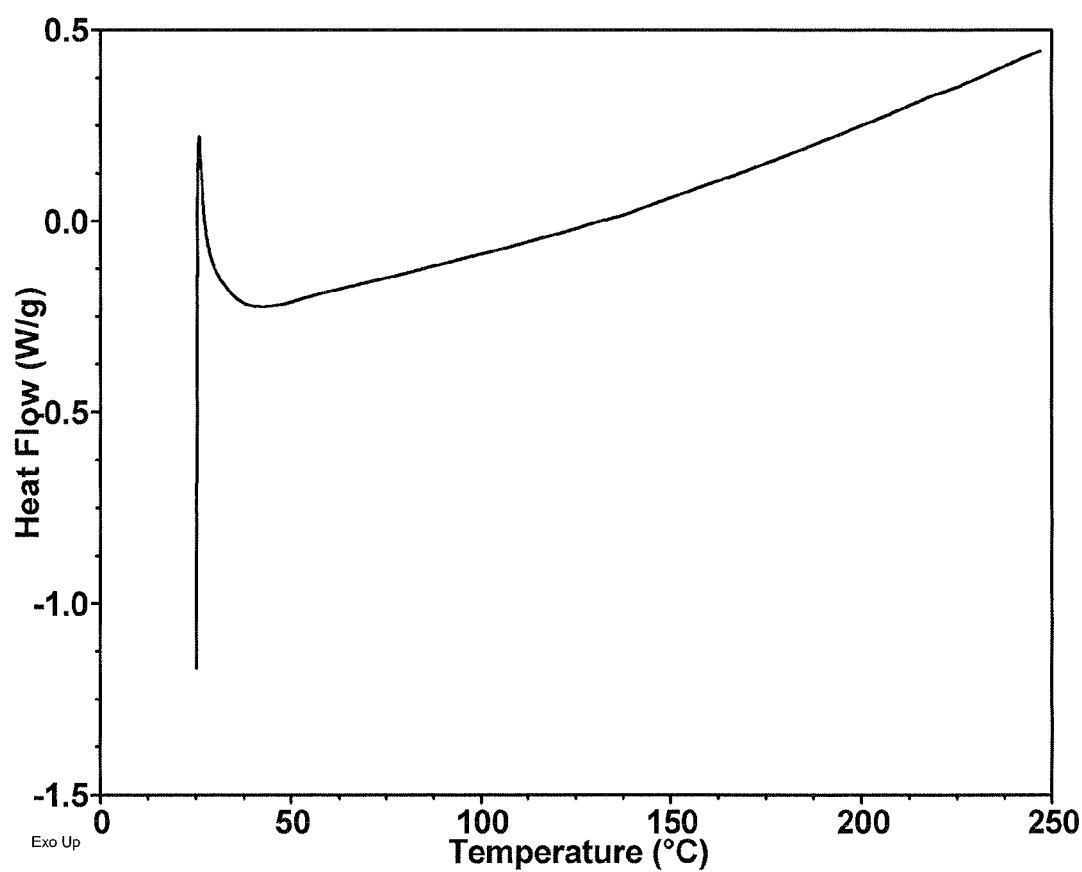
FIG. 9: DSC for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 12:
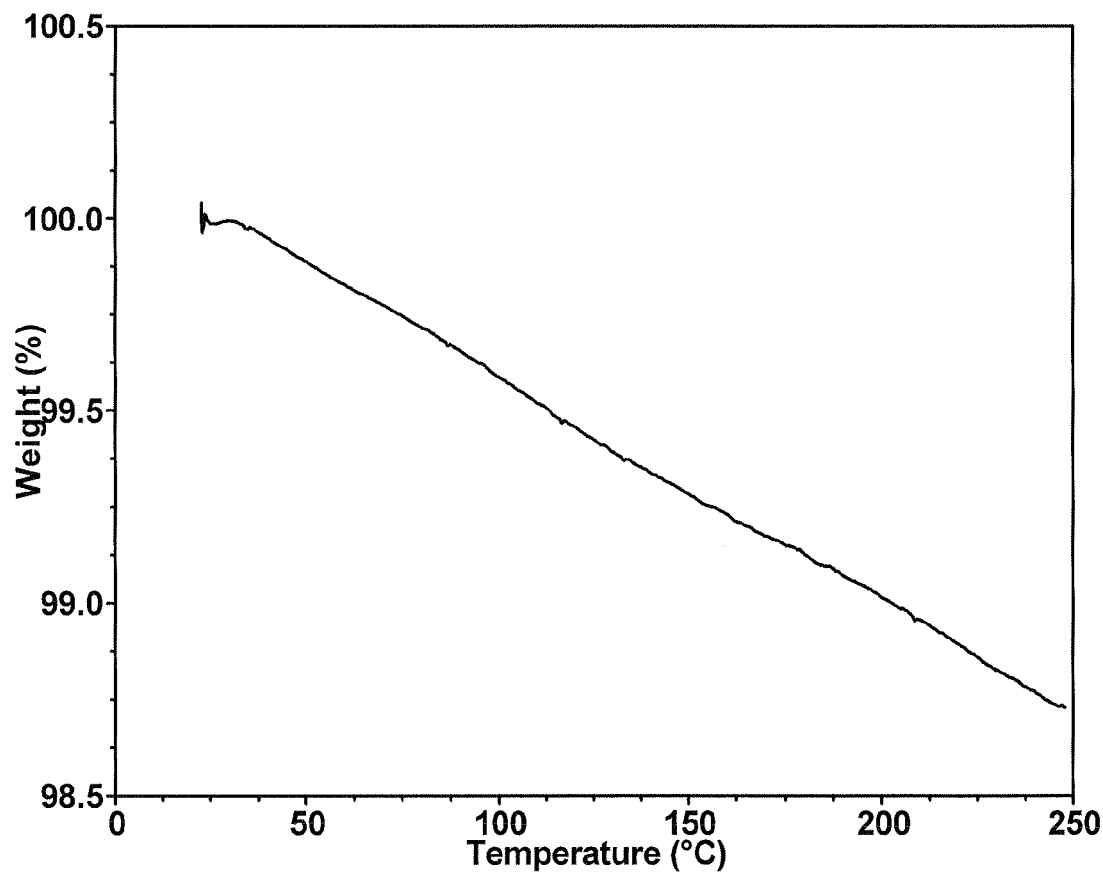
FIG. 12: TGA for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 15:
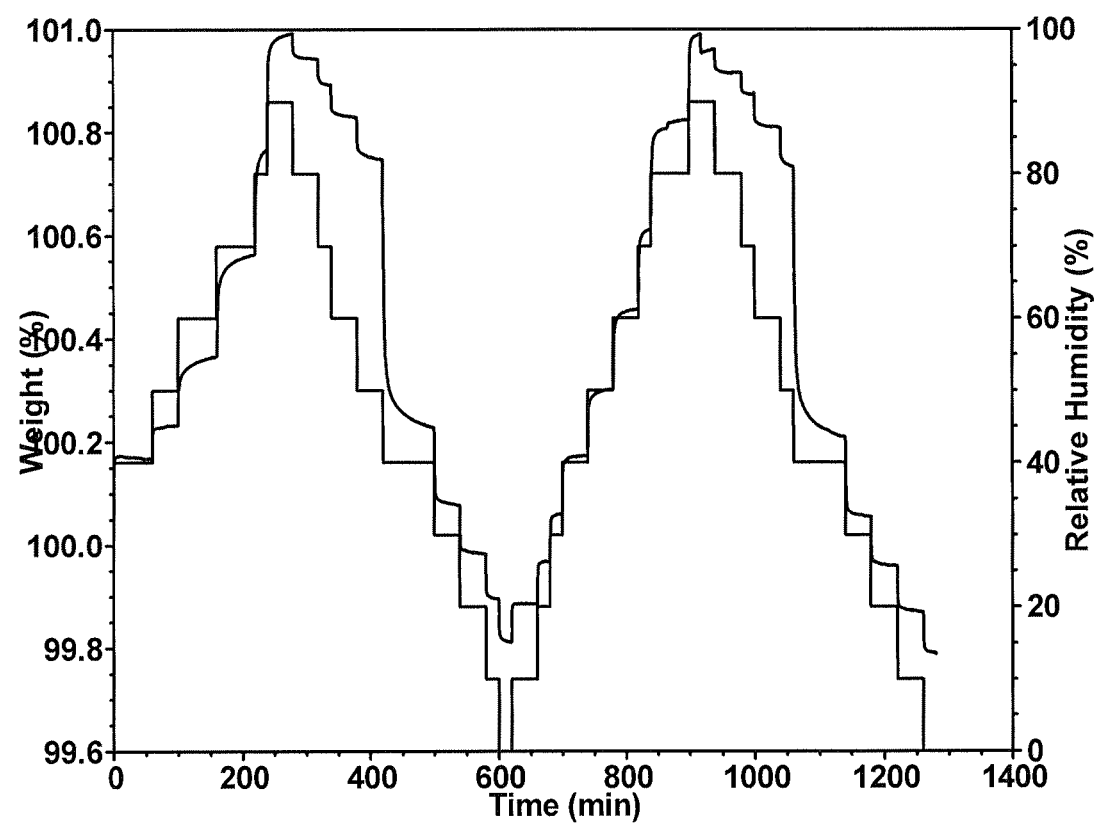
FIG. 15: DVS for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 16:
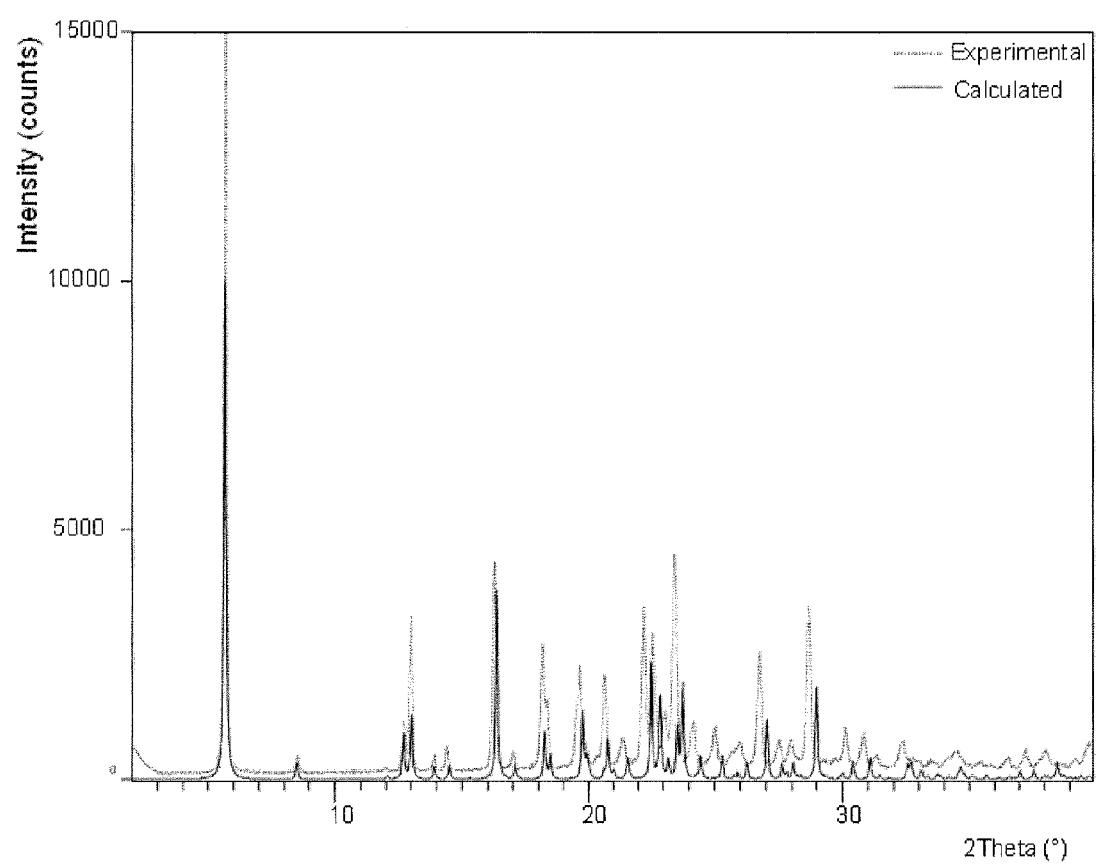
FIG. 16: Calculated and Experimental XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In one embodiment, provided is polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the polymorph exhibits an X-ray powder diffraction (XRPD) pattern substantially as shown in FIG. 5 and/or FIG. 16. Polymorphic sodium Form I may exhibit a differential scanning calorimetry (DSC) thermogram substantially as shown in FIG. 9. Polymorphic sodium Form I may exhibit a thermographic analysis (TGA) graph substantially as shown in FIG. 12. Polymorphic sodium Form I may exhibit dynamic vapour sorption (DVS) graphs substantially as shown in FIG. 15.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

Polymorphic sodium Form I may have a unit cell as determined by crystal X-ray crystallography of the following dimensions: a=8.9561 (10) Å; b=13.9202 (14) Å; c=31.115 (3) Å; α=90°; β=90°; and γ=90°.

In some embodiments of polymorphic sodium Form I, at least one, at least two, at least three, at least four, at least five, at least six, at least seven, at least eight, at least nine, or all of the following (a)-(j) apply: (a) polymorphic Form I has an XRPD pattern substantially as shown in FIG. 5 and/or FIG. 16; (b) polymorphic sodium Form I has a DSC thermogram substantially as shown in FIG. 9; (c) polymorphic sodium Form I has a TGA graph substantially as shown in FIG. 12; (d) polymorphic sodium Form I has DVS graphs substantially as shown in FIG. 15; (e) polymorphic sodium Form I has a unit cell, as determined by crystal X-ray crystallography, of the following dimensions: a=8.9561 (10) Å; b=13.9202 (14) Å; c=31.115 (3) Å; α=90°; β=90°; and γ=90°; (f) polymorphic sodium Form I has an orthorhombic crystal system; (g) polymorphic sodium Form I has a P212121 space group; (h) polymorphic sodium Form I has a volume of 3879.2 Å$^3$; (i) polymorphic Form I has a Z value of 4; and (j) polymorphic Form I has a density of 1.614 Mg/m$^3$.

In some embodiments, polymorphic sodium Form I has at least one, at least two, at least three, at least four, or all of the following properties:
  (a) an XRPD pattern substantially as shown in FIG. 5 and/or FIG. 16;
  (b) a DSC thermogram substantially as shown in FIG. 9;
  (c) TGA graphs substantially as shown in FIG. 12;
  (d) DVS graphs substantially as shown in FIG. 15; and
  (e) a unit cell, as determined by crystal X-ray crystallography, of the following dimensions a=8.9561 (10) Å; b=13.9202 (14) Å; c=31.115 (3) Å; α=90°; β=90°; and γ=90°;

In some embodiments, polymorphic sodium Form I has an XRPD pattern displaying at least two, at least three, at least four, at least five, or at least six of the degree 2θ-reflections with the greatest intensity as the XRPD pattern substantially as shown in FIG. 1 and/or FIG. 8.

In certain embodiments, polymorphic sodium Form I has an XRPD pattern comprising degree 2θ-reflections (+/−0.2 degrees 2θ) at 5.5, 16.1, and 23.3. In one embodiment, polymorphic sodium Form I has an XRPD pattern comprising degree 2θ-reflections (+/−0.2 degrees 2θ) at 5.5, 16.1, and 23.3 and one or more of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and one of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and two of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and three of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, 23.3, 22.1, 28.5, and 22.5. In one embodiment, polymorphic sodium Form I has an XRPD pattern comprising degree 2θ-reflections (+/−0.2 degrees 2θ) at 5.5, 16.1, 23.3, 22.1, 28.5, 22.5, 19.5, and 26.6. In one embodiment, polymorphic sodium Form I has an XRPD pattern comprising any three degree 2θ-reflections (+/−0.2 degrees 2θ) selected from the group consisting of 5.5, 16.1, 23.3, 22.1, 28.5, 22.5, 19.5, 26.6, and 17.9.

Formula III

It is desirable to develop a crystalline form of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate that may be useful in the synthesis of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A form of a potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may be an intermediate to the synthesis of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A polymorphic form or polymorph or cocrystal may have properties such as bioavailability and stability at certain conditions that may be suitable for medical or pharmaceutical uses.

A crystalline form of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide advantages such as: improving the manufacturing process of an active agent or the stability or storability of a drug product form of the compound or an active ingredient, and/or having suitable bioavailability and/or stability as an active agent.

The use of certain solvents has been found to produce different polymorphic forms of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, including any one or more of polymorphic Forms I, II, and III which may exhibit one or more favorable characteristics described above. The processes for the preparation of the polymorphs described herein, and characterization of these polymorphs are described in greater detail below.

The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may be named or identified as potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate under IUPAC.

In particular embodiments, crystalline forms and co-crystals of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are disclosed.

In yet a further embodiment, novel forms of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula III) are disclosed.

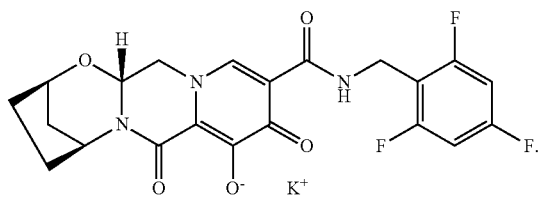

(III)

In yet another embodiment, potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is disclosed.

In yet another embodiment, potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form II is disclosed.

In yet another embodiment, potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form III is disclosed.

In a still other embodiment, hydrated potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate is disclosed.

Formula III, Form I

In one aspect, provided is polymorphic Form I of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

Polymorphic potassium Form I may have a unit cell as determined by crystal X-ray crystallography of the following dimensions: a=32.0409 (11) Å; b=10.2935 (4) Å; c=15.4691 (7) Å; α=90°; β=90°; and γ=90°.

In some embodiments of polymorphic potassium Form I, at least one, at least two, at least three, at least four, at least five, or all of the following (a)-(f) apply: (a) polymorphic potassium Form I has a unit cell, as determined by crystal X-ray crystallography, of the following dimensions: a=32.0409 (11) Å; b=10.2935 (4) Å; c=15.4691 (7) Å;

α=90°; β=90°; and γ=90°; (b) potassium Form I has an orthorhombic crystal system; (c) polymorphic potassium Form I has a P 21 21 2 space group; (d) polymorphic potassium Form I has a volume of 5101.9(4) Å$^3$; (e) polymorphic potassium Form I has a Z value of 8; and (f) potassium Form I has a density of 1.498 Mg/m$^3$.

In some embodiments, polymorphic potassium Form I has the following properties:
  (a) a unit cell, as determined by crystal X-ray crystallography, of the following dimensions a=32.0409 (11) Å; b=10.2935 (4) Å; c=15.4691 (7) Å; α=90°; β=90°; and γ=90°.

Formula III, Form II (Dimer)

In one aspect, provided is polymorphic Form II of potassium (2R,5S,13aR)-7,9-dioxo-10-((2,4,6-trifluorobenzyl) carbamoyl)-2,3,4,5,7,9,13,13a-octahydro-2,5-methano-pyrido[1',2':4,5]pyrazino[2,1-b][1,3]oxazepin-8-olate.

Polymorphic potassium Form II may have a unit cell as determined by crystal X-ray crystallography of the following dimensions: a=32.0285 (17) Å; b=10.3029 (7) Å; c=15.5363 (10) Å; α=90; β=90°; and γ=90°.

In some embodiments of potassium Form II, at least one, at least two, at least three, at least four, at least five, or all of the following (a)-(f) apply: (a) polymorphic potassium Form II has a unit cell, as determined by crystal X-ray crystallography, of the following dimensions: a=32.0285 (17) Å; b=10.3029 (7) Å; c=15.5363 (10) Å; α=90°; β=90°; and γ=90°; (b) polymorphic potassium Form II has an orthorhombic crystal system; (c) polymorphic potassium Form II has a P 21 21 2 space group; (d) polymorphic potassium Form II has a volume of 5126.8(6) Å$^3$; (e) polymorphic potassium Form II has a Z value of 4; and (f) polymorphic potassium Form II has a density of 1.336 Mg/m$^3$.

In some embodiments, polymorphic potassium Form II has the following properties:
  (a) a unit cell, as determined by crystal X-ray crystallography, of the following dimensions a=32.0285 (17) Å; b=10.3029 (7) Å; c=15.5363 (10) Å; α=90°; β=90°; and γ=90°.

Formula III, Form III

In one aspect, provided is polymorphic Form III of potassium (2R,5S,13aR)-7,9-dioxo-10-((2,4,6-trifluorobenzyl)carbamoyl)-2,3,4,5,7,9,13,13a-octahydro-2,5-methano-pyrido[1',2':4,5]pyrazino[2,1-b][1,3]oxazepin-8-olate.

Polymorphic potassium Form III may have a unit cell as determined by crystal X-ray crystallography of the following dimensions: a=8.8412 (3) Å; b=10.8837 (4) Å; c=13.9107 (5) Å; α=71.3620 (1)°; β=76.343 (2)°; and γ=82.943 (2)°.

In some embodiments of polymorphic potassium Form III, at least one, at least two, at least three, at least four, at least five, or all of the following (a)-(f) apply: (a) polymorphic potassium Form III has a unit cell, as determined by crystal X-ray crystallography, of the following dimensions: a=8.8412 (3) Å; b=10.8837 (4) Å; c=13.9107 (5) Å; α=71.3620 (1)°; β=76.343 (2)°; and γ=82.943 (2)°; (b) potassium Form III has a triclinic crystal system; (c) polymorphic potassium Form III has a P1 space group; (d) polymorphic potassium Form III has a volume of 1230.86 (8) Å$^3$; (e) polymorphic potassium Form III has a Z value of 2; and (f) potassium Form III has a density of 1.483 Mg/m$^3$.

In some embodiments, polymorphic potassium Form III has the following properties:
  1. a unit cell, as determined by crystal X-ray crystallography, of the following dimensions a=8.8412 (3) Å; b=10.8837 (4) Å; c=13.9107 (5) Å; α=71.3620 (1)°; β=76.343 (2)°; and γ=82.943 (2)°

Co-Crystals

Formula 1 Citric Acid Co-Crystal

In another embodiment, a citric acid co-crystal of (2R, 5S,13aR)-8-hydroxy-7,9-dioxo-N-(2,4,6-trifluorobenzyl)-2, 3,4,5,7,9,13,13a-octahydro-2,5-methanopyrido[1',2':4,5] pyrazino[2,1-b][1,3]oxazepine-10-carboxamide is disclosed.

In one embodiment, provided is Formula I citric acid co-crystal of (2R,5S,13aR)-8-hydroxy-7,9-dioxo-N-(2,4,6-trifluorobenzyl)-2,3,4,5,7,9,13,13a-octahydro-2,5-methano-pyrido[1',2':4,5]pyrazino[2,1-b][1,3]oxazepine-10-carboxamide.

Formula I citric acid co-crystal may have a unit cell as determined by crystal X-ray crystallography of the following dimensions: a=7.4315 (6) Å; b=15.5755 (13) Å; c=15.6856 (13) Å; α=88.784 (2)°; β=77.029 (2)°; and γ=76.832 (2)°.

In some embodiments of Formula I citric acid co-crystal, at least one, at least two, at least three, at least four, at least five, or all of the following (a)-(g) apply: (a) Formula I citric acid co-crystal has a unit cell, as determined by crystal X-ray crystallography, of the following dimensions: a=7.4315 (6) Å; b=15.5755 (13) Å; c=15.6856 (13) Å; α=88.784 (2)°; β=77.029 (2)°; and γ=76.832 (2)°; (b) Formula I citric acid co-crystal has a triclinic crystal system; (c) Formula I citric acid co-crystal has a P1 space group; (d) Formula I citric acid co-crystal has a volume of 1721.9(2) Å$^3$; (e) Formula I citric acid co-crystal has a Z value of 2; and (f) Formula I citric acid co-crystal has a density of 1.608 Mg/m$^3$.

In some embodiments, Formula I citric acid co-crystal has all of the following properties:
  (a) a unit cell, as determined by crystal X-ray crystallography, of the following dimensions a=7.4315 (6) Å; b=15.5755 (13) Å; c=15.6856 (13) Å; α=88.784 (2)°; β=77.029 (2)°; and γ=76.832 (2)°.

Formula 1 Fumaric Acid Co-Crystal

In a certain embodiment, a fumaric acid co-crystal of (2R,5S,13aR)-8-hydroxy-7,9-dioxo-N-(2,4,6-trifluoroben-zyl)-2,3,4,5,7,9,13,13a-octahydro-2,5-methanopyrido[1',2': 4,5]pyrazino[2,1-b][1,3]oxazepine-10-carboxamide is disclosed.

In one aspect, provided is Formula I fumaric acid co-crystal of (2R,5S,13aR)-8-hydroxy-7,9-dioxo-N-(2,4,6-trifluorobenzyl)-2,3,4,5,7,9,13,13a-octahydro-2,5-methano-pyrido[1',2':4,5]pyrazino[2,1-b][1,3]oxazepine-10-carboxamide.

Formula I fumaric acid co-crystal may have a unit cell as determined by crystal X-ray crystallography of the following dimensions: a=26.767 (5) Å; b=8.2313 (14) Å; c=24.089 (4) Å; α=90°; β=99.283 (4)°; and γ=90°.

In some embodiments of Formula I fumaric acid co-crystal, at least one, at least two, at least three, at least four, at least five, or all of the following (a)-(f) apply: (a) Formula I fumaric acid co-crystal has a unit cell, as determined by crystal X-ray crystallography, of the following dimensions: a=26.767 (5) Å; b=8.2313 (14) Å; c=24.089 (4) Å; α=90°; β=99.283 (4)°; and γ=90°; (b) Formula I fumaric acid co-crystal has a monoclinic crystal system; (c) Formula I fumaric acid co-crystal has a C2 space group; (d) Formula I fumaric acid co-crystal has a volume of 5237.9(16) Å$^3$; (e) Formula I fumaric acid co-crystal has a Z value of 8; and (f) Formula I fumaric acid co-crystal has a density of 1.503 Mg/m$^3$.

In some embodiments, Formula I fumaric acid co-crystal has all of the following properties:

(a) a unit cell, as determined by crystal X-ray crystallography, of the following dimensions a=26.767 (5) Å; b=8.2313 (14) Å; c=24.089 (4) Å; α=90°; β=99.283 (4)°; and γ=90°.

Formula 1 Oxalic Acid Co-Crystal

In yet another embodiment, a oxalic acid co-crystal of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is disclosed.

In one embodiment, provided is Formula I oxalic acid co-crystal of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Formula I oxalic acid co-crystal may have a unit cell as determined by crystal X-ray crystallography of the following dimensions: a=7.8562 (3) Å; b=14.5031 (5) Å; c=19.9756 (7) Å; α=90°; β=101.291 (2)°; and γ=90°.

In some embodiments of Formula I oxalic acid co-crystal, at least one, at least two, at least three, at least four, at least five, or all of the following (a)-(f) apply: (a) Formula I oxalic acid co-crystal has a unit cell, as determined by crystal X-ray crystallography, of the following dimensions: a=7.8562 (3) Å; b=14.5031 (5) Å; c=19.9756 (7) Å; α=90°; β=101.291 (2)°; and γ=90°; (b) Formula I oxalic acid co-crystal has a monoclinic crystal system; (c) Formula I oxalic acid co-crystal has a P2(1) space group; (d) Formula I oxalic acid co-crystal has a volume of 2231.95(14) Å$^3$; (e) Formula I oxalic acid co-crystal has a Z value of 4; and (f) Formula I oxalic acid co-crystal has a density of 1.604 g/cm$^3$.

In some embodiments, Formula I oxalic acid co-crystal has the following properties:
(a) a unit cell, as determined by crystal X-ray crystallography, of the following dimensions a=7.8562 (3) Å; b=14.5031 (5) Å; c=19.9756 (7) Å; α=90°; β=101.291 (2)°; and γ=90°.

In certain embodiments, Formula I oxalic acid co-crystal has an XRPD pattern comprising degree 2θ-reflections (+/−0.2 degrees 2θ) at 19.1, 14.5, and 9.1. In one embodiment, Formula I oxalic acid co-crystal has an XRPD pattern comprising degree 2θ-reflections (+/−0.2 degrees 2θ) at 19.1, 14.5, and 9.1 and one or more of the degree 2θ-reflections (+/−0.2 degrees 2θ) at 7.6, 26.5, and 17.1. In one embodiment, Formula I oxalic acid co-crystal has an XRPD pattern comprising degree 2θ-reflections (+/−0.2 degrees 2θ) at 19.1, 14.5, and 9.1 and one of the degree 2θ-reflections (+/−0.2 degrees 2θ) at 7.6, 26.5, and 17.1. In one embodiment, Formula I oxalic acid co-crystal has an XRPD pattern comprising degree 2θ-reflections (+/−0.2 degrees 2θ) at 19.1, 14.5, and 9.1 and two of the degree 2θ-reflections (+/−0.2 degrees 2θ) at 7.6, 26.5, and 17.1. In one embodiment, Formula I oxalic acid co-crystal has an XRPD pattern comprising degree 2θ-reflections (+/−0.2 degrees 2θ) at 19.1, 14.5, and 9.1 and three of the degree 2θ-reflections (+/−0.2 degrees 2θ) at 7.6, 26.5, and 17.1. In one embodiment, Formula I oxalic acid co-crystal has an XRPD pattern comprising degree 2θ-reflections (+/−0.2 degrees 2θ) at 19.1, 14.5, 9.1, 7.6, 26.5, and 17.1. In one embodiment, Formula I oxalic acid co-crystal has an XRPD pattern comprising degree 2θ-reflections (+/−0.2 degrees 2θ) at 19.1, 14.5, 9.1, 7.6, 26.5, 17.1, 21.8, and 39.4. In one embodiment, polymorphic Formula I oxalic acid co-crystal has an XRPD pattern comprising any three degree 2θ-reflections (+/−0.2 degrees 2θ) selected from the group consisting of 19.1, 14.5, 9.1, 7.6, 26.5, 17.1, 21.8, 39.4, 29.7, and 11.6.

Pharmaceutical Compositions

For the purposes of administration, in certain embodiments, the compounds described herein are administered as a raw chemical or are formulated as pharmaceutical compositions. Pharmaceutical compositions of the present invention comprise a compound of Formulas (I), (II) or (III), including forms and co-crystals thereof, and a pharmaceutically acceptable carrier, diluent or excipient. The compound of Formulas (I), (II), or (III) is present in the composition in an amount which is effective to treat a particular disease or condition of interest. The activity of compounds of Formulas (I), (II), and (III) can be determined by one skilled in the art, for example, as described in co-pending U.S. application Ser. No. 14/133,855, filed Dec. 19, 2013 entitled "POLYCYCLIC-CARBAMOYLPYRIDONE COMPOUNDS AND THEIR PHARMACEUTICAL USE". The activity of compounds of Formulas (I), (II), and (III) can also be determined by one skilled on the art, for example, as described in co-pending PCT Serial No. US2013/076367, filed Dec. 19, 2013 entitled, "POLYCYCLIC-CARBAMOYLPYRIDONE COMPOUNDS AND THEIR PHARMACEUTICAL USE." Appropriate concentrations and dosages can be readily determined by one skilled in the art. In certain embodiments, a compound of Formulas (I), (II), and/or (III) is present in the pharmaceutical composition in an amount from about 25 mg to about 500 mg. In certain embodiments, a compound of Formulas (I), (II), and/or (III) is present in the pharmaceutical composition in an amount of about 100 mg to about 300 mg. In certain embodiments, a compound of Formulas (I), (II), and/or (III) is present in the pharmaceutical composition in an amount of about 5 mg to about 100 mg. In certain embodiments, a compound of Formulas (I), (II), and/or (III) is present in the pharmaceutical composition in an amount of about 25 mg to about 100 mg. In certain embodiments, a compound of Formulas (I), (II), and/or (III) is present in the pharmaceutical composition in an amount of about 50 mg to about 100 mg. In certain embodiments, a compound of Formula (I), (II), and/or (III) is present in the pharmaceutical composition in an amount of about 5 mg, 25 mg, 50 mg, 75, mg, 100 mg, 200 mg, 300 mg, 400 mg or about 500 mg.

Formula I

Provided are also compositions comprising at least one, at least two, at least three, at least four, at least five, at least six, at least seven, or all of polymorphs (e.g., any one or more of Formula I polymorphic Forms I, II, III, IV, V, VI, VII, and VIII) as described herein. In a particular embodiment, a composition comprising one of Formula I polymorphic Forms I, II, III, IV, V, VI, VII, and VIII described herein is provided. In a particular embodiment, a composition comprising two of Formula I polymorphic Forms I, II, III, IV, V, VI, VII, and VIII described herein is provided. In a particular embodiment, a composition comprising three of Formula I polymorphic Forms I, II, III, IV, V, VI, VII, and VIII described herein is provided. In a particular embodiment, a composition comprising four of Formula I polymorphic Forms I, II, III, IV, V, VI, VII, and VIII described herein is provided. In a particular embodiment, a composition comprising five of Formula I polymorphic Forms I, II, III, IV, V, VI, VII, and VIII described herein is provided. In a particular embodiment, a composition comprising six of Formula I polymorphic Forms I, II, III, IV, V, VI, VII, and VIII described herein is provided. In a particular embodiment, a composition comprising seven of Formula I polymorphic Forms I, II, III, IV, V, VI, VII, and VIII described herein is provided. In a particular embodiment, a composition comprising eight of Formula I polymorphic Forms I, II, III, IV, V, VI, VII, and VIII described herein is provided. In other embodiments, the compositions described herein may comprise substantially pure polymorphic forms, or may be substantially free of other polymorphs and/or impurities.

In some embodiments, the composition comprises a polymorphic form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. In certain embodiments are provided compositions comprising a polymorphic form as described herein, wherein the (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide within the composition is substantially pure (i.e., substantially pure Form I, Form II, Form III, Form IV, Form V, Form VI or Form VII or Form VIII). In particular embodiments of compositions comprising a polymorphic form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, at least about 50%, at least about 60%, at least about 70%, at least about 80%, at least about 85%, at least about 90%, at least about 95%, at least about 96%, at least about 97%, at least about 98%, or at least about 99% of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide present in the composition is one of the polymorphic forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the polymorphic forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In other embodiments of compositions comprising a polymorphic form disclosed herein, less than about 50%, less than about 40%, less than about 30%, less than about 20%, less than about 10%, less than about 5%, less than about 4%, less than about 3%, less than about 2% or less than about 1% of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide present in the composition are other polymorphs of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide and/or impurities.

In yet other embodiments of compositions comprising the polymorphic forms disclosed herein, impurities make up less than about 5%, less than about 4%, less than about 3%, less than about 2% or less than about 1% of the total mass relative to the mass of the polymorphic forms present. Impurities may, for example, include by-products from synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, contaminants, degradation products, other polymorphic forms, amorphous form, water, and solvents. In certain embodiments, impurities include by-products from the process of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. In certain embodiments, impurities include contaminants from the process of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

In certain embodiments, impurities include degradation products of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. In certain embodiments, impurities include other polymorphic forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. In certain embodiments, impurities include water or solvent. In certain embodiments of compositions comprising a polymorphic form disclosed herein, impurities are selected from the group consisting of by-products from synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, contaminants, degradation products, other polymorphic forms, water, solvents and combinations thereof.

In yet other embodiments, the composition comprising a polymorphic form disclosed herein has less than about 5%, less than about 4%, less than about 3%, less than about 2%, or less than about 1% by weight of amorphous or non-crystalline (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

Formula II

Provided are also compositions comprising at least one polymorph (e.g., any one or more of Formula II polymorphic Forms I) as described herein. In a particular embodiment, a composition comprising Formula II polymorphic Form I, described herein is provided. In other embodiments, the compositions described herein may comprise substantially pure polymorphic forms, or may be substantially free of other polymorphs and/or impurities.

In some embodiments, the composition comprises a polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments are provided compositions comprising a polymorphic form as described herein, wherein the sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate within the composition is substantially pure (i.e., substantially pure Form I). In particular embodiments of compositions comprising a polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, at least about 50%, at least about 60%, at least about 70%, at least about 80%, at least about 85%, at least about 90%, at least about 95%, at least about 96%, at least about 97%, at least about 98%, or at least about 99% of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate present in the composition is Formula II, Form I, disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form I of sodium (2R,5S,13aR)-7,9-dioxo-10-((2,4,6- trifluorobenzyl)carbamoyl)-2,3,4,5,7,9,13,13a-octahydro-2,5-methanopyrido[1',2':4,5]pyrazino[2,1-b][1,3]oxazepin-8-olate.

In other embodiments of compositions comprising a polymorphic form disclosed herein, less than about 50%, less than about 40%, less than about 30%, less than about 20%, less than about 10%, less than about 5%, less than about 4%, less than about 3%, less than about 2% or less than about 1% of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate present in the composition are other polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate and/or impurities.

In yet other embodiments of compositions comprising the polymorphic forms disclosed herein, impurities make up less than about 5%, less than about 4%, less than about 3%, less than about 2% or less than about 1% of the total mass relative to the mass of the polymorphic forms present. Impurities may, for example, include by-products from synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, amorphous form, water, and solvents. In certain embodiments, impurities include by-products from the process of synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include contaminants from the process of synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include degradation products of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include other polymorphic forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include water or solvent. In certain embodiments of compositions comprising a polymorphic form disclosed herein, impurities are selected from the group consisting of by-products from synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, water, solvents and combinations thereof.

In yet other embodiments, the composition comprising Formula II, Form I disclosed herein has less than about 5%, less than about 4%, less than about 3%, less than about 2%, or less than about 1% by weight of amorphous or non-crystalline sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In some embodiments, the term "substantially pure" or "substantially free" with respect to a particular polymorphic form of a compound means that the composition comprising the polymorphic form contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including other polymorphic forms and/or impurities. In certain embodiments, "substantially pure" or "substantially free of" refers to a substance free of other substances, including other polymorphic forms and/or impurities. Impurities may, for example, include by-products or left over reagents from chemical reactions, contaminants, degradation products, other polymorphic forms, water, and solvents.

Formula III

Provided are also compositions comprising at least one, or all of polymorphs (e.g., any one or more of Formula III polymorphic Forms I, II, and III) as described herein. In a particular embodiment, a composition comprising one of Formula III polymorphic Forms I, II, and III described herein is provided. In a particular embodiment, a composition comprising two of Formula IIII polymorphic Forms I, II, and III described herein is provided. In other embodiments, the compositions described herein may comprise substantially pure polymorphic forms, or may be substantially free of other polymorphs and/or impurities.

In some embodiments, the composition comprises a polymorphic form of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments are provided compositions comprising a polymorphic form as described herein, wherein the potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate within the composition is substantially pure (i.e., substantially pure Form I, II, and/or III). In particular embodiments of compositions comprising a polymorphic form of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, at least about 50%, at least about 60%, at least about 70%, at least about 80%, at least about 85%, at least about 90%, at least about 95%, at least about 96%, at least about 97%, at least about 98%, or at least about 99% of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate present in the composition is one of the polymorphic forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the polymorphic forms potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In other embodiments of compositions comprising a polymorphic form disclosed herein, less than about 50%, less than about 40%, less than about 30%, less than about 20%, less than about 10%, less than about 5%, less than about 4%, less than about 3%, less than about 2% or less than about 1% of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate present in the composition are other polymorphs of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate and/or impurities.

In yet other embodiments of compositions comprising the polymorphic forms disclosed herein, impurities make up less than about 5%, less than about 4%, less than about 3%, less than about 2% or less than about 1% of the total mass relative to the mass of the polymorphic forms present. Impurities may, for example, include by-products from synthesizing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, water, and solvents. In certain embodiments, impurities include by-products from the process of synthesizing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include contaminants from the process of synthesizing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include degradation products of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include other polymorphic forms of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include water or solvent. In certain embodiments of compositions comprising a polymorphic form disclosed herein, impurities are selected from the group consisting of by-products from synthesizing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, water, solvents and combinations thereof.

In yet other embodiments, the composition comprising a polymorphic form disclosed herein has less than about 5%, less than about 4%, less than about 3%, less than about 2%, or less than about 1% by weight of amorphous or non-crystalline potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

Provided are also compositions comprising at least one, at least two, at least three, at least four, at least five, at least six, at least seven, at least eight, at least nine, at least ten, or all of polymorphs (e.g., any one or more of Formula I polymorphic Forms I, II, III, IV, V, VI, VII, and VIII, Formula II polymorphic Form I, and/or Formula III polymorphic Forms I, II, and III) as described herein. In a particular embodiment, a composition comprising one of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising two of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising three of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising four of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising five of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising six of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising seven of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising eight of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising nine of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising ten of Formula I polymorphic Forms I, II, III, IV, V, VI, VII, and VIII, Formula II polymorphic Form I, and/or Formula III polymorphic Forms I, II, and III described herein is provided. In a particular embodiment, a composition comprising eleven of Formula I polymorphic Forms I, II, III, IV, V, VI, VII, and VIII, Formula II polymorphic Form I, and/or Formula III polymorphic Forms I, II, and III described herein is provided. In other embodiments, the compositions described herein may comprise substantially pure polymorphic forms, or may be substantially free of other polymorphs and/or impurities.

In some embodiments, the term "substantially pure" or "substantially free" with respect to a particular polymorphic form of a compound means that the composition comprising the polymorphic form contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including other polymorphic forms and/or impurities. In certain embodiments, "substantially pure" or "substantially free of" refers to a substance free of other substances, including other polymorphic forms and/or impurities. Impurities may, for example, include by-products or left over reagents from chemical reactions, contaminants, degradation products, other polymorphic forms, water, and solvents.

Administration of the compounds of the invention in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral, sublingual, buccal, rectal, vaginal, and intranasal. In one embodiment, the pharmaceutical compositions is prepared for oral administration. In a specific embodiment, the pharmaceutical composition is a tablet. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention for treatment of a disease or condition of interest in accordance with the teachings of this invention.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

For example, a solid pharmaceutical composition intended for oral administration can be prepared by mixing a compound of the invention with at least one suitable pharmaceutical excipient to form a solid preformulation composition, which then may be readily subdivided into equally effective unit dosage forms such as tablets, pills and capsules. Accordingly, in one embodiment, a pharmaceutical composition is provided, which includes a compound of Formula (I), (II), or (III) and a pharmaceutical excipient.

The compounds of the invention are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents once or twice daily for as long as the patient is infected, latently infected, or to prevent infection (e.g. for multiple years, months, weeks, or days).

Combination Therapy

In one embodiment, a method for treating or preventing an HIV infection in a human having or at risk of having the infection is provided, comprising administering to the human a therapeutically effective amount of a compound disclosed herein in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein in combination with a therapeutically effective amount of one or more (e.g., one, two, three, one or two, or one to three) additional therapeutic agents.

In one embodiment, a method for treating an HIV infection in a human having or at risk of having the infection is provided, comprising administering to the human a therapeutically effective amount of a compound or composition disclosed herein in combination with a therapeutically effective amount of one or more (e.g., one, two, three, one or two, or one to three) additional therapeutic agents.

In certain embodiments, the present invention provides a method for treating an HIV infection, comprising administering to a patient in need thereof a therapeutically effective amount of a compound or composition disclosed herein in combination with a therapeutically effective amount of one or more additional therapeutic agents which are suitable for treating an HIV infection.

One embodiment provides a compound disclosed herein in combination with one or more (e.g., one, two, three, one or two, or one to three) additional therapeutic agents for use in a method for treating or preventing an HIV infection in a human having or at risk of having the infection. One embodiment provides a compound disclosed herein in combination with one or more (e.g., one, two, three, one or two, or one to three) additional therapeutic agents for use in a method for treating an HIV infection in a human having or at risk of having the infection. One embodiment provides a compound disclosed herein for use in a method for treating or preventing an HIV infection in a human having or at risk of having the infection, wherein the compound is administered in combination with one or more (e.g., one, two, three, one or two, or one to three) additional therapeutic agents. One embodiment provides a compound disclosed herein for use in a method for treating an HIV infection in a human having or at risk of having the infection, wherein the compound is administered in combination with one or more (e.g., one, two, three, one or two, or one to three) additional therapeutic agents. In certain embodiments, the present invention provides a compound disclosed herein in combination with one or more additional therapeutic agents which are suitable for treating an HIV infection, for use in a method for treating an HIV infection. In certain embodiments, the present invention provides a compound disclosed herein for use in a method for treating an HIV infection, wherein the compound is administered in combination with one or more additional therapeutic agents which are suitable for treating an HIV infection.

One embodiment provides the use of a compound disclosed herein thereof, in combination with one or more (e.g., one, two, three, one or two, or one to three) additional therapeutic agents in the manufacture of a medicament for treating or preventing an HIV infection in a human having or at risk of having the infection. One embodiment provides the use of a compound disclosed herein in combination with one or more (e.g., one, two, three, one or two, or one to three) additional therapeutic agents in the manufacture of a medicament for treating an HIV infection in a human having or at risk of having the infection. One embodiment provides the use of a compound disclosed herein in the manufacture of a medicament for treating or preventing an HIV infection in a human having or at risk of having the infection, wherein the compound is administered in combination with one or more (e.g., one, two, three, one or two, or one to three) additional therapeutic agents. One embodiment provides the use of a compound disclosed herein thereof, in the manufacture of a medicament for treating an HIV infection in a human having or at risk of having the infection, wherein the compound is administered in combination with one or more (e.g., one, two, three, one or two, or one to three) additional therapeutic agents. In certain embodiments, the present invention provides the use of a compound disclosed herein thereof, in combination with one or more additional therapeutic agents which are suitable for treating an HIV infection, in treating an HIV infection. In certain embodiments, the present invention provides the use of a compound disclosed herein thereof for treating an HIV infection, wherein the compound is administered in combination with one or more additional therapeutic agents which are suitable for treating an HIV infection.

A compound as disclosed herein (e.g., any compound of Formulas (I), (II), and/or (III)) may be combined with one or more additional therapeutic agents in any dosage amount of the compound of Formulas (I), (II), and/or (III) (e.g., from 50 mg to 1000 mg of compound).

In one embodiment, pharmaceutical compositions comprising a compound disclosed herein in combination with one or more (e.g., one, two, three, one or two, or one to three) additional therapeutic agents, and a pharmaceutically acceptable carrier, diluent or excipient are provided.

In one embodiment, combination pharmaceutical agents comprising a compound disclosed herein in combination with one or more (e.g., one, two, three, one or two, or one to three) additional therapeutic agents are provided.

In one embodiment, kits comprising a compound disclosed herein in combination with one or more (e.g., one, two, three, one or two, or one to three) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof.

In other embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists,), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, HIV gene therapy, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formulas (I), (II), and/or (III) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof. In certain embodiments, the tablet can contain one or more active ingredients for treating HIV, such as HIV nucleoside or nucleotide inhibitors of reverse transcriptase. In certain embodiments, such tablets are suitable for once daily dosing.

In further embodiments, the additional therapeutic agent is selected from one or more of:
(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirine, BILR 355 BS, VRX 840773, lersivirine (UK-453061), RDEA806, KM023 and MK-1439;

(3) HIV nucleoside or nucleotide inhibitors of reverse transcriptase selected from the group consisting of zidovudine, emtricitabine, didanosine, stavudine, zalcitabine, lamivudine, abacavir, abacavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences), fosalvudine tidoxil (formerly HDP 99.0003), tenofovir, tenofovir disoproxil fumarate, tenofovir alafenamide, tenofovir alafenamide hemifumarate, tenofovir alafenamide fumarate (Gilead Sciences), GS-7340 (Gilead Sciences), GS-9148 (Gilead Sciences), adefovir, adefovir dipivoxil, CMX-001 (Chimerix) and CMX-157 (Chimerix);

(4) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir, dolutegravir sodium, and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and (15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), and combinations thereof.

In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® or EVIPLERA® (rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, dolutegravir+rilpivirine hydrochloride, atazanavir sulfate+cobicistat, atazanavir+cobicistat, darunavir+cobicistat, efavirenz+lamivudine+tenofovir disoproxil fumarate, tenofovir alafenamide hemifumarate+emtricitabine+cobicistat+elvitegravir, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Kivexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), doravirine+lamivudine+tenofovir disoproxil fumarate, doravirine+lamivudine+tenofovir disoproxil, tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;
(7) HIV gp41 inhibitors selected from the group consisting of enfuvirtide, sifuvirtide and albuvirtide;
(8) HIV entry inhibitors selected from the group consisting of cenicriviroc;
(9) HIV gp120 inhibitors selected from the group consisting of Radha-108 (Receptol) and BMS-663068;
(10) CCR5 inhibitors selected from the group consisting of aplaviroc, vicriviroc, maraviroc, cenicriviroc, PRO-140, Adaptavir (RAP-101), nifeviroc (TD-0232), TD-0680, and vMIP (Haimipu);
(11) CD4 attachment inhibitors selected from the group consisting of ibalizumab;
(12) CXCR4 inhibitors selected from the group consisting of plerixafor, ALT-1188, vMIP and Haimipu;
(13) Pharmacokinetic enhancers selected from the group consisting of cobicistat and ritonavir;
(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;
(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine (Novartis), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR, ETV-01, CDX-1401, rcAd26.MOS1.HIV-Env and DNA-Ad5 gag/pol/nef/nev (HVTN505);
(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523 and VRC07;
(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;
(18) HIV nucleocapsid p7 (NCp7) inhibitors selected from the group consisting of azodicarbonamide;
(19) HIV maturation inhibitors selected from the group consisting of BMS-955176 and GSK-2838232;
(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and
(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, HIviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone, AAV-eCD4-Ig gene therapy and PA-1050040 (PA-040);
and combinations thereof.

In certain embodiments, a compound disclosed herein is combined with two, three, four or more additional therapeutic agents. In certain embodiments, a compound disclosed herein is combined with two additional therapeutic agents. In other embodiments, a compound disclosed herein is combined with three additional therapeutic agents. In further embodiments, a compound disclosed herein is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein is combined with an HIV nucleoside or nucleotide inhibitor of reverse transcriptase and an HIV non-nucleoside inhibitor of reverse transcriptase. In another specific embodiment, a compound disclosed herein is combined with an HIV nucleoside or nucleotide inhibitor of reverse transcriptase, and an HIV protease inhibiting compound. In a further embodiment, a compound disclosed herein is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein is combined with two HIV nucleoside or nucleotide inhibitors of reverse transcriptase.

In certain embodiments, a compound disclosed herein, is combined with one, two, three, four or more additional therapeutic agents. In certain embodiments, a compound disclosed herein is combined with one additional therapeutic agent. In certain embodiments, a compound disclosed herein is combined with two additional therapeutic agents. In other embodiments, a compound disclosed herein is combined with three additional therapeutic agents. In further embodiments, a compound disclosed herein is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein is combined with an HIV nucleoside or nucleotide inhibitor of reverse transcriptase and an HIV non-nucleoside inhibitor of reverse transcriptase. In another specific embodiment, a compound disclosed herein is combined with an HIV nucleoside or nucleotide inhibitor of reverse transcriptase, and an HIV protease inhibiting compound. In a further embodiment, a compound disclosed herein is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein is combined with at least one HIV nucleoside inhibitor of reverse transcriptase, an integrase inhibitor, and a pharmacokinetic enhancer. In another embodiment, a compound disclosed herein is combined with two HIV nucleoside or nucleotide inhibitors of reverse transcriptase.

In certain embodiments, a compound disclosed herein is combined with at least one HIV nucleoside inhibitor of reverse transcriptase, an integrase inhibitor, and a pharmacokinetic enhancer.

In a particular embodiment, a compound disclosed herein is combined with abacavir, abacavir sulfate, tenofovir, tenofovir disoproxil fumarate, tenofovir alafenamide, or tenofovir alafenamide hemifumarate.

In a particular embodiment, a compound disclosed herein is combined with tenofovir, tenofovir disoproxil fumarate, tenofovir alafenamide, or tenofovir alafenamide hemifumarate.

In a particular embodiment, a compound disclosed herein is combined with a first additional therapeutic agent selected from the group consisting of: abacavir, abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine.

In a particular embodiment, a compound disclosed herein is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In a particular embodiment, a compound disclosed herein is combined with one, two, three, four or more additional therapeutic agents selected from Triumeq® (dolutegravir+abacavir+lamivudine), dolutegravir+abacavir sulfate+lamivudine, raltegravir, raltegravir+lamivudine, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, atazanavir sulfate+cobicistat, atazanavir+cobicistat, darunavir+cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir_sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, darunavir+cobicistat, atazanavir sulfate+cobicistat, atazanavir+cobicistat, tenofovir alafenamide and tenofovir alafenamide hemifumarate.

In a particular embodiment, a compound disclosed herein is combined with abacavir, abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein is combined with tenofovir, tenofovir disoproxil, tenofovir disoproxil fumarate, tenofovir alafenamide, or tenofovir alafenamide hemifumarate.

In a particular embodiment, a compound disclosed herein is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein is combined with 5-30 mg tenofovir alafenamide fumarate, tenofovir alafenamide hemifumarate, or tenofovir alafenamide and 200 mg emtricitabine. In certain embodiments, a compound disclosed herein is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein is combined with 10 mg tenofovir alafenamide fumarate, tenofovir alafenamide hemifumarate, or tenofovir alafenamide and 200 mg emtricitabine. In certain embodiments, a compound disclosed herein is combined with 25 mg tenofovir alafenamide fumarate, tenofovir alafenamide hemifumarate, or tenofovir alafenamide and 200 mg emtricitabine. A compound as disclosed herein (e.g., a compound of Formulas (I), (II), and/or (III)) may be combined with the agents provided herein in any dosage amount of the compound (e.g., from 50 mg to 500 mg of compound) the same as if each combination of dosages were specifically and individually listed.

In certain embodiments, a compound disclosed herein is combined with 200-400 mg tenofovir disproxil, tenofovir disoproxil fumarate, or tenofovir disoproxil hemifumarate and 200 mg emtricitabine. In certain embodiments, a compound disclosed herein is combined with 200-250; 200-300; 200-350; 250-350; 250-400; 350-400; 300-400; or 250-400 mg tenofovir disoproxil, tenofovir disoproxil fumarate, or tenofovir disoproxil hemifumarate and 200 mg emtricitabine. In certain embodiments, a compound disclosed herein is combined with 300 mg tenofovir disoproxil fumarate, tenofovir disoproxil hemifumarate, or tenofovir disoproxil and 200 mg emtricitabine. A compound as disclosed herein (e.g., a compound of Formulas (I), (II), and/or (III)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

XRPD Data

In certain embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7−0.3, i.e., about 8.4. Depending on the sample preparation techniques, the calibration techniques applied to the instruments, human operational variation, and etc, those skilled in the art recognize that the appropriate error of margins for a XRPD can be ±0.5; ±0.4; ±0.3; ±0.2; ±0.1; ±0.05; or less. In certain embodiments of the invention, the XRPD margin of error is ±0.2.

Additional details of the methods and equipment used for the XRPD analysis are described in the Examples section.

The XRPD peaks for the crystalline forms of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I) Form I is below in Table 1A.

TABLE 1A

XRPD peaks for crystalline forms of Formula I Form I
Formula I
Form I

| Peak Position [°2θ] | Relative Intensity [%] |
|---|---|
| 9.3 | 6.4 |
| 10.5 | 43.7 |
| 11.4 | 12.6 |
| 13.1 | 96.7 |
| 13.9 | 33.0 |
| 16.2 | 79.4 |
| 17.4 | 48.0 |
| 20.6 | 93.1 |
| 22.3 | 42.0 |
| 25.0 | 81.5 |
| 27.4 | 100.0 |

The XRPD peaks for the crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I) Form II is below in Table 1B.

TABLE 1B

XRPD peaks for crystalline forms of Formula I Form II
Formula I
Form II

| Peak Position [°2θ] | Relative Intensity [%] |
|---|---|
| 6.6 | 100.0 |
| 10.6 | 59.3 |
| 12.5 | 30.6 |
| 14.3 | 14.9 |
| 16.2 | 19.3 |
| 21.4 | 65.1 |
| 23.5 | 10.6 |
| 25.6 | 11.9 |

The XRPD peaks for the crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I) Form III is below in Table 1C.

TABLE 1C

XRPD peaks for crystalline forms of Formula I Form III
Formula I
Form III

| Peak Position [°2θ] | Relative Intensity [%] |
|---|---|
| 9.6 | 56.7 |
| 12.1 | 19.1 |
| 14.0 | 26.2 |
| 16.2 | 17.6 |
| 18.5 | 74.6 |
| 20.0 | 100.0 |
| 22.5 | 35.4 |
| 25.0 | 19.2 |
| 27.0 | 18.0 |
| 29.0 | 14.0 |

The XRPD peaks for the crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I) Form IV is below in Table 1D.

TABLE 1D

XRPD peaks for crystalline forms of Formula I Form IV
Formula I
Form IV

| Peak Position [°2θ] | Relative Intensity [%] |
|---|---|
| 6.2 | 96.1 |
| 8.6 | 40.0 |
| 13.2 | 22.0 |
| 16.3 | 100.0 |
| 18.7 | 32.7 |
| 20.0 | 33.1 |
| 22.3 | 72.9 |
| 22.7 | 76.2 |
| 25.8 | 44.1 |
| 27.7 | 30.3 |

The XRPD peaks for the crystalline form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate (Formula II) is below in Table 1E.

TABLE 1E

XRPD peaks for crystalline forms of Formula II Form I
Formula II
Form I

| Peak Position [°2θ] | Relative Intensity [%] |
|---|---|
| 5.5 | 100.0 |
| 16.1 | 87.3 |
| 17.9 | 22.4 |
| 19.5 | 38.0 |
| 22.1 | 61.8 |
| 22.5 | 42.2 |
| 23.3 | 60.4 |
| 26.6 | 27.3 |
| 28.5 | 42.9 |

The XRPD peaks for the crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide oxalic acid co-crystal Form I is below in Table 1F.

TABLE 1F

XRPD peaks for crystalline forms of
Formula I Oxalic Acid Co-crystal Form I
Formula I
Oxalic Acid
Co-crystal
Form I

| Peak Position [°2θ] | Relative Intensity [%] |
|---|---|
| 7.6 | 16.5 |
| 9.1 | 39.4 |
| 11.6 | 13.6 |
| 14.5 | 94.8 |
| 17.1 | 51.1 |
| 19.1 | 100.0 |
| 21.8 | 40.7 |
| 26.5 | 54.8 |
| 29.7 | 30.4 |
| 39.4 | 37.1 |

Preparation of the Polymorphs
Formula I

One method of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (e.g. a compound of Formula (I)) has been previously described in PCT Publication No. WO2014/100323. This reference is hereby incorporated herein by reference in its entirety, and specifically with respect to the synthesis of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide.

For example, in one aspect, provided is a method of producing a composition comprising one or more polymorphs of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining a compound of Formula (I) with a suitable solvent or a mixture of suitable solvents to produce a composition comprising one or more polymorphs of the compound of Formula (I). In another aspect, provided is another method of producing a composition comprising one or more polymorphs of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a suitable solvent or a mixture of suitable solvents.

The choice of a particular solvent or combination of solvents affects the formation favoring one polymorphic form of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide over another. Solvents suitable for polymorph formation may include, for example, methanol, ethanol, water, isopropyl acetate, acetonitrile, tetrahydrofuran, methyl isobutyl ketone, and any mixtures thereof.

In another aspect, provided is also one or more polymorphs of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced according to any of the methods described herein.

It should be understood that the methods for preparing the polymorphs described herein (including any one or more of polymorphic Forms I to VIII) may yield quantity and quality differences compared to the methods for preparing (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced on laboratory scale.

Formula I, Forms I and II

In one embodiment, provided is a method of producing a composition comprising polymorphic Form I, Form II, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent to produce a composition comprising polymorphic Form I, Form II, or a mixture thereof, of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is isopropyl acetate.

Provided is a polymorphic Form I, Form II, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent, wherein the solvent is isopropyl acetate.

Formula I, Form III

In one embodiment, provided is a method of producing a composition comprising polymorphic Form III of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent to produce a composition comprising polymorphic Form III of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is methyl isobutyl ketone.

Provided is a polymorphic Form III of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent, wherein the solvent is methyl isobutyl ketone.

Formula I, Forms IV, VII, and VIII

In one embodiment, provided is a method of producing a composition comprising polymorphic Form IV, Form VII, and Form VIII, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent to produce a composition comprising polymorphic Form IV, Form VII, and Form VIII, or a mixture thereof, of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is methanol.

Provided is a polymorphic Form IV, Form VII, and Form VIII, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent, wherein the solvent is methanol.

Formula I, Form V

In one embodiment, provided is a method of producing a composition comprising polymorphic Form V of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent to produce a composition comprising polymorphic Form V of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is water.

Provided is a polymorphic Form V of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent, wherein the solvent is water.

Formula I, Form VI

In one embodiment, provided is a method of producing a composition comprising polymorphic Form VI of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent to produce a composition comprising polymorphic Form VI of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is selected from the group consisting of methanol, water, and any mixtures thereof. In an embodiment, the solvent is a mixture of water and methanol.

Provided is a polymorphic Form VI of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a solvent, wherein the solvent is selected from the group consisting of methanol, water, and any mixtures thereof. In an embodiment, the solvent is a mixture of water and methanol.

Formula II

One method of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (e.g. a compound of Formula (I)) has been previously described in PCT Publication No. WO2014/100323. This reference is hereby incorporated herein by reference in its entirety, and specifically with respect to the synthesis of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. One method of synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate (e.g. a compound of Formula (II)) is described herein.

For example, in one aspect, provided is a method of producing a composition comprising one or more polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining a compound of Formula (II) with a suitable solvent or a mixture of suitable solvents to produce a composition comprising one or more polymorphs of the compound of Formula (II). In another aspect, provided is another method of producing a composition comprising one or more polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate with a suitable solvent or a mixture of suitable solvents.

The choice of a particular solvent or combination of solvents affects the formation favoring one polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate over another. Solvents suitable for polymorph formation may include, for example, methanol, ethanol, water, isopropyl acetate, acetonitrile, tetrahydrofuran, methyl isobutyl ketone, and any mixtures thereof.

In another aspect, provided is also one or more polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate produced according to any of the methods described herein.

It should be understood that the methods for preparing the polymorphs described herein (including any polymorphic Form I) may yield quantity and quality differences compared to the methods for preparing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate produced on laboratory scale.

Formula II, Form I

In one embodiment, provided is a method of producing a composition comprising polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a sodium base (e.g. sodium hydroxide) in a solvent to produce a composition comprising polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the solvent is selected from the group consisting of ethanol, dimethylformamide, and any mixture thereof. In an embodiment, the solvent is a mixture of ethanol and dimethylformamide.

Provided is also polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate prepared by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a sodium base (e.g. sodium hydroxide) in a solvent, wherein the solvent is selected from the group consisting of ethanol, dimethylformamide, and any mixture thereof. In an embodiment, the solvent is a mixture of ethanol and dimethylformamide.

Formula III

One method of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (e.g. a compound of Formula (I)) has been previously described in PCT Publication No. WO2014/100323. This reference is hereby incorporated herein by reference in its entirety, and specifically with respect to the synthesis of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. One method of synthesizing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate (e.g. a compound of Formula (III)) is described herein.

For example, in one aspect, provided is a method of producing a composition comprising one or more polymorphs of potassium (2R,5S,13aR)-7,9-dioxo-10-((2,4,6- trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining a compound of Formula (III) with a suitable solvent or a mixture of suitable solvents to produce a composition comprising one or more polymorphs of the compound of Formula (III). In another aspect, provided is another method of producing a composition comprising one or more polymorphs of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate with a suitable solvent or a mixture of suitable solvents.

The choice of a particular solvent or combination of solvents affects the formation favoring one polymorphic form of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate over another. Solvents suitable for polymorph formation may include, for example, methanol, ethanol, water, isopropyl acetate, acetonitrile, tetrahydrofuran, methyl isobutyl ketone, and any mixtures thereof.

In another aspect, provided is also one or more polymorphs of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate produced according to any of the methods described herein.

It should be understood that the methods for preparing the polymorphs described herein (including any one or more of polymorphic Forms I-III) may yield quantity and quality differences compared to the methods for preparing potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate produced on laboratory scale.

Formula III, Form I

In one embodiment, provided is a method of producing a composition comprising polymorphic Form I of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium acetate) in a solvent to produce a composition comprising polymorphic Form I of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the solvent is selected from the group consisting of ethanol, water, and any mixtures thereof. In an embodiment, the solvent is a mixture of ethanol and water.

Provided is also polymorphic Form I of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate prepared by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium acetate) in a solvent, wherein the solvent is selected from the group consisting of ethanol, water, and any mixtures thereof.

Formula III, Form II

In one embodiment, provided is a method of producing a composition comprising polymorphic Form II of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium acetate) in a solvent to produce a composition comprising polymorphic Form II of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the solvent is selected from the group consisting of acetonitrile, water, and any mixtures thereof. In an embodiment, the solvent is a mixture of acetonitrile and water.

Provided is also polymorphic Form II of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate prepared by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium acetate) in a solvent, wherein the solvent is selected from the group consisting of acetonitrile, water, and any mixtures thereof.

Formula III, Form III

In one embodiment, provided is a method of producing a composition comprising polymorphic Form III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium phosphate) in a solvent to produce a composition comprising polymorphic Form III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the solvent is methanol.

Provided is also polymorphic Form III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate prepared by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a potassium base (e.g. potassium phosphate) in a solvent, wherein the solvent is methanol.

Formula I Co-Crystals

In one embodiment, provided is a method of producing a composition comprising polymorphic citric acid co-crystal, fumaric acid co-crystal, oxalic acid co-crystal, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with an acid (e.g. citric acid, fumaric acid, or oxalic acid) in a solvent to produce a composition comprising polymorphic citric acid co-crystal, fumaric acid co-crystal, oxalic acid co-crystal, or a mixture thereof, of the (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the solvent is tetrahydrofuran.

Provided is a polymorphic citric acid co-crystal, fumaric acid co-crystal, oxalic acid co-crystal, or a mixture thereof, of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide produced by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with an acid (e.g. citric acid, fumaric acid, or oxalic acid) in a solvent, wherein the solvent is tetrahydrofuran.

Uses in Manufacturing of Drug Product

Formula I

Provided are also a use of the polymorphs described herein in the manufacture of a drug product. The one or more of the polymorphic forms described herein (e.g., one or more of polymorphic Forms I, II, III, IV, V, VI, VII, and VIII) may be used as an intermediate in the manufacturing process to produce the drug product.

In certain embodiments, Forms I to VIII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide are used in the manufacture of an active pharmaceutical ingredient. In certain embodiments, Form I of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form II of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form III of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form IV of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form V of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form VI of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form VII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient. In certain embodiments, Form VIII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide is used in the manufacture of an active pharmaceutical ingredient.

Formula II

Provided are also a use of the polymorphs described herein in the manufacture of a drug product. The one or more of the polymorphic forms described herein (e.g., polymorphic Form I) may be used as an intermediate in the manufacturing process to produce the drug product.

In certain embodiments, Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are used in the manufacture of an active pharmaceutical ingredient.

Formula III

Provided are also a use of the polymorphs described herein in the manufacture of a drug product. The one or more of the polymorphic forms described herein (e.g., one or more of polymorphic Forms I, II, and III) may be used as an intermediate in the manufacturing process to produce the drug product.

In certain embodiments, Forms I-III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are used in the manufacture of an active pharmaceutical ingredient. In certain embodiments, Form I of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate is used in the manufacture of an active pharmaceutical ingredient. In certain embodiments, Form II of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate is used in the manufacture of an active pharmaceutical ingredient. In certain embodiments, Form III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate is used in the manufacture of an active pharmaceutical ingredient.

Articles of Manufacture and Kits

Compositions comprising one or more of the polymorphic forms described herein (e.g., one or more of polymorphic Forms I to VIII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide; polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate; and polymorphic Forms I, II, and III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate) and formulated in one or more pharmaceutically acceptable carriers, excipients or other ingredients can be prepared, placed in an appropriate container, and labeled for treatment of an indicated condition. Accordingly, there also is contemplated an article of manufacture, such as a container comprising a dosage form of one or more of the polymorphic forms described herein (e.g., one or more of polymorphic Forms I to VIII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide; polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate; and polymorphic Forms I, II, and III of potassium (2R,5S,13aR)-7,9-dioxo-10-((2,4,6-trifluorobenzyl)carbamoyl)-2,3,4,5,7,9,13,13a- octahydro-2,5-methanopyrido[1',2':4,5]pyrazino[2,1-b][1,3]oxazepin-8-olate), and a label containing instructions for use of the compound(s).

In some embodiments, the article of manufacture is a container comprising a dosage form of one or more of the polymorphic forms described herein (e.g., one or more of polymorphic Forms I to VIII of (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide; polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate; and polymorphic Forms I, II, and III of potassium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate), and one or more pharmaceutically acceptable carriers, excipients or other ingredients. In one embodiment of the articles of manufacture described herein, the dosage form is a tablet.

Kits also are contemplated. For example, a kit can comprise a dosage form of a pharmaceutical composition and a package insert containing instructions for use of the composition in treatment of a medical condition. The instructions for use in the kit may be for treating HIV. In certain embodiments, the instructions for use in the kit may be for treating HIV.

In certain embodiments, the polymorphic, salt, co-crystal and solvate forms described herein may potentially exhibit improved properties. For example, in certain embodiments, the polymorphic, salt, co-crystal and solvate forms described herein may potentially exhibit improved stability. Such improved stability could have a potentially beneficial impact on the manufacture of the Compound of Formulas I, II, and/or III, such as for example offering the ability to store process intermediate for extended periods of time. Improved stability could also potentially benefit a composition or pharmaceutical composition of the Compound of Formulas I, II, and/or III. In certain embodiments, the polymorphic, salt and solvate forms described herein may also potentially result in improved yield of the Compound of Formulas I, II, and/or III, or potentially result in an improvement of the quality of the Compound of Formulas I, II, and/or III. In certain embodiments, the polymorphic, salt and solvate forms described herein may also exhibit improved pharmacokinetic properties and/or potentially improved bioavailability.

Methods

Formula I Form I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (73 mg) was added to a glass vial. Isopropanol (1 mL) was added, the vial was capped, and the suspension was stirred at about 21° C. for not less than 5 days. Formula I Form I was isolated as a solid from the suspension by centrifuge/filtration and characterized as discussed below.

Formula I Form II (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (60 mg) was added to a glass vial. Methyl tert-butyl ether (1 mL) was added, the vial was capped, and the suspension was stirred at about 21° C. for not less than 5 days. Formula I Form II was isolated as a solid from the suspension by centrifuge/filtration and characterized as discussed below.

(2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (98 mg) was suspended in ethanol/water (1 mL, aw 0.7-0.8) for 5 days with agitation. Formula I Form II was isolated as a solid from the suspension by centrifuge/filtration and characterized as discussed below.

Formula I Form III from Compound G-1a

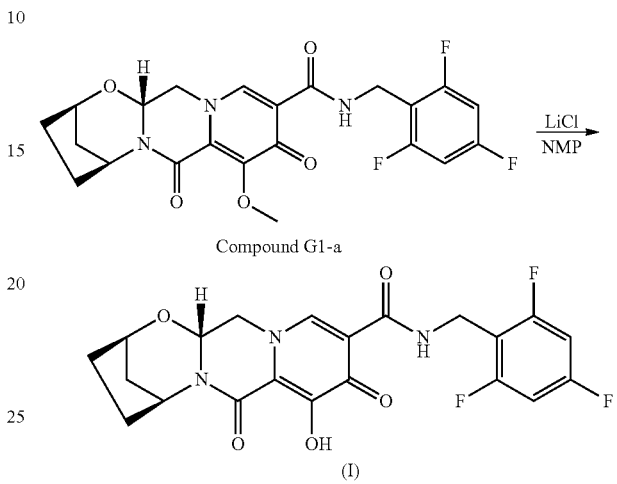

Compound G1-a

A solution of about 10% (w/w) Compound G-1a (2.5 g Compound 1001) in methylene chloride was concentrated to a residue under vacuum. LiCl (2.6 g, 7 equiv) followed by N-methyl-2-pyrrolidone (12.5 mL) was added to the resulting residue. The method of preparing compound G1-a can be determined by one skilled on the art, for example, as described in co-pending PCT Serial No. US2013/076367, filed Dec. 19, 2013 entitled, "POLYCYCLIC-CARBAMOYLPYRIDONE COMPOUNDS AND THEIR PHARMACEUTICAL USE." The mixture was heated to an internal temperature of approximately 75° C. After 2.5 hours, the reaction was cooled to approximately 20° C. Dichloromethane (12.5 mL) and 0.5M hydrochloric acid (12.5 mL) was added, and the resulting mixture stirred for 5 minutes. The phases were separated, and the organic layer was washed with 10% aqueous sodium chloride solution (twice) followed by water. This solution was concentrated while gradually adding 3 volumes of isopropyl alcohol portionwise (40° C. bath temperature, 200-230 torr vacuum). The resulting slurry was slowly cooled to 2-4° C. The product was filtered and deliquored and dried. Formula I Form III was isolated and characterized as discussed below.

Formula I Form III from Formula I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (100 mg) and ethanol (0.5 mL) were added to a reaction vessel and seeded with Formula I Form III. The slurry was allowed to age at room temperature for about 18 hours. Formula I Form III was isolated as a solid from the suspension by centrifuge/filtration and characterized as discussed below.

Formula I Form IV (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (406 mg) and potassium acetate (200 mg) were added to a glass vial. Methanol (5 mL) was added, the vial was capped, and the suspension was stirred at about 21° C. After 11 days the solids were isolated from the suspension by centrifuge/filtration and the filtrate retained. After slow evaporation over 16 days, large crystals of Formula I Form IV were found in the filtrate vessel.

Formula I Form V 25.2 mg (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) was mixed with 1.21 grams of water at room temperature, forming a solution. After several days, crystals suitable for single crystal X-ray crystallography were found and analyzed.

Formula I Form VI 173 mg of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) was suspended in 2 mL of methanol/water solution ($a_w$ 0.5). The suspension was filtered the next day and several days after that, crystals suitable for single crystal X-ray crystallography were found in the filtrate and analyzed.

Formula I Form VII 112.3 mg (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) suspended in 0.95 grams of methanol at room temperature. A sample of the suspension was filtered for testing after several days, and several days post-filtration, solids suitable for single crystal X-ray crystallography were found in the filtrate and analyzed.

Formula I Form VIII 5.3 g (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) suspended in 80 mL of methanol at room temperature. To the mixture was slowly added 0.70 grams of KOH dissolved in 20 mL methanol. Full addition of KOH solution resulted in a solution. A suspension formed over the course of two days and a sample was filtered for testing after ten days. After several days, solids suitable for single crystal X-ray crystallography were found in the filtrate and analyzed.

Formula II Form I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (20 g) and ethanol (80 mL) were added to a reaction vessel and warmed to about 75° C. Aqueous sodium hydroxide (22 mL 2 M solution) was added over approximately 30 minutes, after which the slurry was cooled to approximately 20° C. over approximately one hour. Sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was collected by filtration, washed with EtOH (50 mL) and dried under vacuum.

1H NMR (400 MHz, DMSO-d6) δ 10.63 (t, J=5.8 Hz, 1H), 7.88 (s, 1H), 7.29-7.07 (m, 2H), 5.20 (dd, J=8.6, 3.6 Hz, 1H), 5.09 (t, J=4.1 Hz, 1H), 4.52 (m, 3H), 4.35 (dd, J=12.8, 3.6 Hz, 1H), 3.87 (dd, J=12.7, 8.7 Hz, 1H), 2.03-1.80 (m, 3H), 1.76-1.64 (m, 2H), 1.50-1.40 (m, 1H).

Formula I Citric Acid Co-Crystal Form I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (131 mg) and citric acid (148 mg) were added to a glass vial. Tetrahydrofuran (1 mL) was added, the vial was capped, and the mixture was stirred at about 21° C. for two days. The vial was vented and the solvent was allowed to evaporate at about 21° C. unassisted. After eight weeks at room temperature, crystals were found in the vessel and were identified as a 1:2 Formula I citric acid co-crystal.

Formula I Fumaric Acid Co-Crystal Form I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (131 mg) and fumaric acid (103 mg) were added to a glass vial. Tetrahydrofuran (1 mL) was added, the vial capped, and the suspension stirred at about 21° C. for two days. An additional 1 mL of tetrahydrofuran was added, and the mixture was heated to 45° C. After about 12 hours at 45° C. the mixture was found to be fully dissolved and was removed from the heat bath. The vial was vented, and the solvent left to evaporate at room temperature. After one day solids were observed in the vial and it was re-capped. After eight weeks large crystals were found in the capped vial and identified as a 1:1 Formula I fumaric acid co-crystal.

Formula I Oxalic Acid Co-Crystal Form I (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (147 mg) and oxalic acid (134 mg) were added to a glass vial. Tetrahydrofuran (1 mL) was added, the vial capped, and the resulting solution was stirred at about 21° C. for about two days. The vessel was vented, and the solvent was allowed to evaporate at room temperature unassisted. After one day solids were observed in the vial and it was re-capped. Two days later large crystals were found in the vial and were identified as a 1:1 Formula I oxalic acid co-crystal.

Formula III Form I 406 mg of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) was combined with 200 mg potassium acetate and 5 mL of methanol at room temperature, resulting in a suspension. A sample of the suspension was filtered the next day for testing. After several days, solids suitable for single crystal X-ray crystallography were found in the filtrate and analyzed.

(2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (1.96 g) was charged to a reaction flask and stirred, followed by ethanol (20 mL). The mixture was stirred at room temperature resulting in a suspension. In a separate vessel potassium hydroxide (253 mg) was dissolved in deionized water (5 mL). The potassium hydroxide solution was transferred by syringe pump to the stirring suspension over about 2.5 hours followed by a rinse into the reactor with water (2 mL) after the base solution transfer was completed.

A sample of about 0.5 mL of the resulting suspension was centrifuge/filtered. The filtrate was retained and stored at room temperature. After several weeks it had evaporated and the vessel contained large crystals, which were identified by single x-ray crystallography as Formula III Form II.

Formula III Form II (Dimer)

94.8 mg of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (25.2 mg) was suspended in 1 mL of acetonitrile/water (1:1). After one week a sample was filtered for testing. After several days, solids suitable for single crystal X-ray crystallography were found in the filtrate and analyzed.

Formula III Form III

A 4 mL glass vial was charged with 140 mg of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, and 73 mg of potassium phosphate and 2 mL of methanol. The vial was capped and placed in a rotating mixer to provide gentle and constant mixing. The experiment was carried out at room temperature. More than a week later and more than a month later solids were isolated by centrifuge/filtration and examined by XRPD. Large crystals suitable for Single Crystal X-ray Crystallography were found and analyzed.

The crystalline forms of the present invention were characterized by various analytical techniques, including X-ray powder diffraction (XRPD), differential scanning calorimetry (DSC), thermogravimetric analysis (TGA), and dynamic vapor sorption (DVS) using the procedures described below.

X-Ray Powder Diffraction:

XRPD analysis was conducted on a diffractometer (PANanalytical XPERT-PRO, PANanalytical B.V., Almelo, Netherlands) using copper radiation (Cu Kα, λ=1.5418 Å). Samples were prepared for analysis by depositing the powdered sample in the center of an aluminum holder equipped with a zero background plate. The generator was operated at a voltage of 45 kV and amperage of 40 mA. Slits used were Soller 0.02 rad., antiscatter 1.00, and divergence. The sample rotation speed was 2 sec. Scans were performed from 2 to 40° 2θ during 15 min with a step size of 0.0167° 2θ. Data analysis was performed by X'Pert Highscore version 2.2c (PANalytical B.V., Almelo, Netherlands) and X'Pert data viewer version 1.2d (PANalytical B.V., Almelo, Netherlands).

The XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I is represented in FIG. 1.

The XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form II is represented in FIG. 2.

The XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III is represented in FIG. 3.

The XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form IV is represented in FIG. 4.

The XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 5. The calculated XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I represented in FIG. 5 was calculated by using Mercury 3.1 Development (Build RC5). Single crystal data for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was input into Mercury 3.1 Development (Build RC5) to calculate the XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I. Bulk material, such as stoichiometry arity between the temperature was obtained on a Rigaku Miniflex II XRD using power settings of 40 kV, 15 mA, scan speed of 2.0000 degrees per minute, a Miniflex 300/600 goniometer and an ASC-6 attachment, a scan range of 3.000 to 40.000 degrees, an incident slit of 1.250 degrees, a length limiting slit of 10.0 mm, and SC-70 detector, a receiving slit #1 of 1.250 degrees, continuous scan mode, and a receiving slit #2 of 0.3 mm. The sample was prepared by smoothing about 20 mg of solids on a silicon disk mounted in a metal holder. Acquisition temperature was ~21° C.

The XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[11',2':4,5]pyrazino[2,1-b][1,3]oxazepin-8-olate Form I is further represented in FIG. 16. The calculated XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I represented in FIG. 16 was calculated by using Mercury 3.1 Development (Build RC5). Single crystal data for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was input into Mercury 3.1 Development (Build RC5) to calculate the XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I. Bulk material, such as stoichiometry arity between the temperature was obtained on a Rigaku Miniflex II XRD using power settings of 40 kV, 15 mA, scan speed of 2.0000 degrees per minute, a Miniflex 300/600 goniometer and an ASC-6 attachment, a scan range of 3.000 to 40.000 degrees, an incident slit of 1.250 degrees, a length limiting slit of 10.0 mm, and SC-70 detector, a receiving slit #1 of 1.250 degrees, continuous scan mode, and a receiving slit #2 of 0.3 mm. The sample was prepared by smoothing about 20 mg of solids on a silicon disk mounted in a metal holder. Acquisition temperature was ~21° C.

FIG. 16 compares the calculated XRPD pattern of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I to the experimental XRPD pattern of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I. The comparison shows the degree to which the calculated XRPD and experimental XRPD agree. Strong agreement indicates the solved crystal structure is also the crystal structure of the material analyzed directly by XRPD. This determination can support orthogonal data about the composition of the bulk material, such as stoichiometry.

Figure 6:
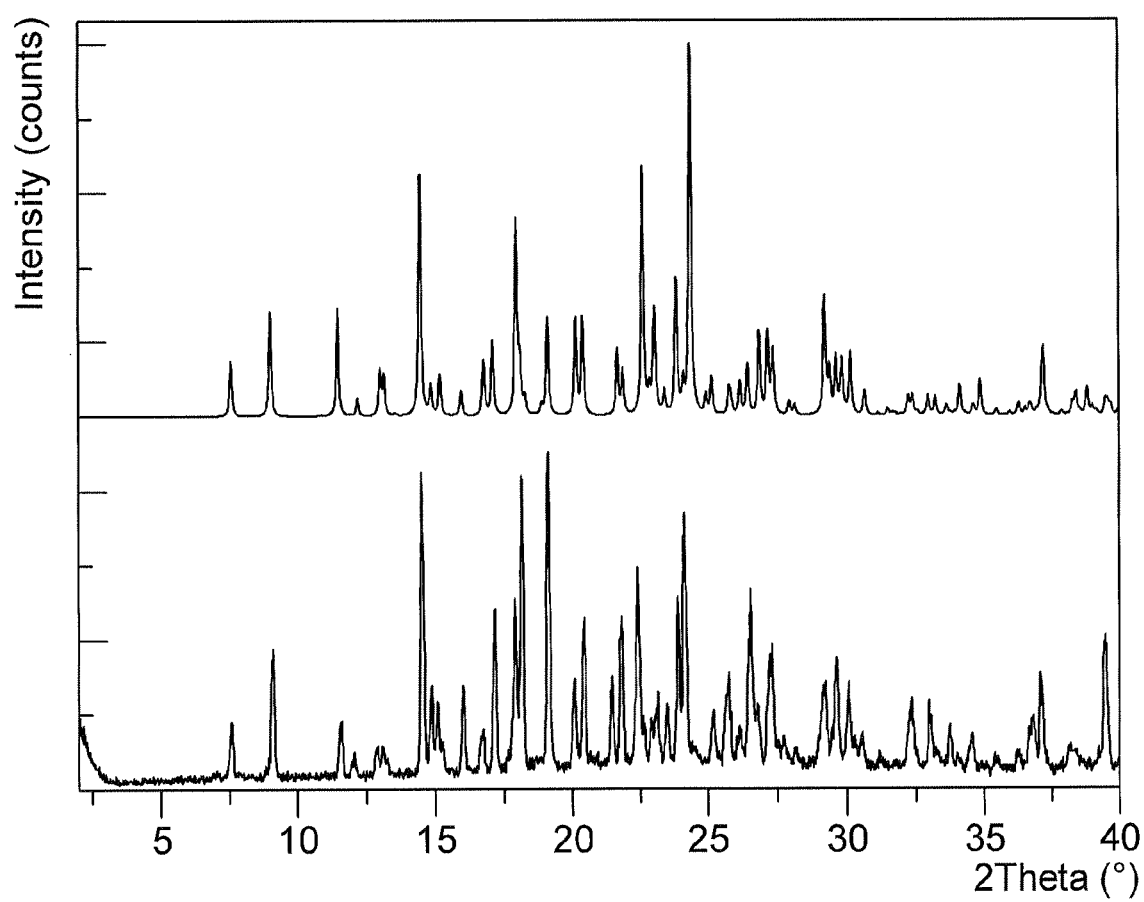
FIG. 6: Actual and calculated XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide oxalic acid co-crystal Form I.

The actual and calculated XRPD pattern for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide oxalic acid co-crystal Form I is represented in FIG. 6.

Differential Scanning Calorimetry:

Thermal properties were evaluated using a Differential Scanning Calorimetry (DSC) instrument (TA Q1000, TA Instruments, New Castle, Del., USA). Approximately 1 to 10 mg of solid sample was placed in a standard aluminum pan vented with a pinhole for each experiment and heated at a rate of 5 to 10° C./min under a 50 mL/min nitrogen purge. Data analysis was conducted using Universal Analysis 2000 Version 4.7A (TA Instruments, New Castle, Del., USA).

Heat of fusion analysis was conducted by sigmoidal integration of the endothermic melting peak.

The DSC for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I is represented in FIG. 7.

The DSC for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III is represented in FIG. 8.

The DSC for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 9.

Thermogravimetric Analysis:

Thermogravimetric analysis (TGA) was performed on a TGA instrument (TA Q500, TA Instruments, New Castle, Del., USA). Approximately 1 to 10 mg of solid sample was placed in an open aluminum pan for each experiment and heated at a rate of 5 to 10° C./min under a 60 mL/min nitrogen purge using. Data analysis was conducted using Universal Analysis 2000 Version 4.7A (TA Instruments, New Castle, Del., USA).

The TGA for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I is represented in FIG. 10.

The TGA for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III is represented in FIG. 11.

The TGA for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 12.

Dynamic Vapor Sorption:

The hygroscopicity was evaluated at room temperature using a dynamic vapor sorption (DVS) instrument (TGA Q5000 TA Instruments, New Castle, Del.). Water adsorption and desorption were studied as a function of relative humidity (RH) over the range of 0 to 90% at 25° C. The relative humidity in the chamber was increased by 10% RH and held until the so lid and atmosphere reached equilibration. The equilibrium test was continued until passed or expired after 5 or 10 hours. At this point, RH was raised 10% higher and the process was repeated until 90% RH was reached and equilibrated. During this period, the water sorption was monitored. For desorption, the relative humidity was decreased in a similar manner to measure a full sorption/desorption cycle. The cycle was optionally repeated. All experiments were operated in dm/dt mode (mass variation over time) to determine the equilibration endpoint. Approximately 5-10 mg of solid was used. Data analysis was conducted using Universal Analysis 2000 Version 4.7A (TA Instruments, New Castle, Del., USA).

The DVS for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form I is represented in FIG. 13.

The DVS for (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III is represented in FIG. 14.

The DVS for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 15.

The single crystal X-ray diffraction studies were carried out on a Bruker APEX II Ultra diffractometer equipped with Mo $K_\alpha$ radiation (e.g. Wavelength). Crystals of the subject compound were cut into a 0.22×0.18×0.04 mm section and mounted on a Cryoloop with Paratone-N oil. Data were collected in a nitrogen gas stream at a particular temperature as shown in the Tables below (e.g. 100(2) K or 200(2) K). A total number of reflections were collected covering the indices, (e.g. $-9<=h<=10, -13<=k<=16, -37<=l<=36$). Certain reflections were found to be symmetry independent, with a $R_{int}$ value. Indexing and unit-cell refinement indicated a crystal system (e.g. monoclinic, triclinic, or orthorhombic lattice). The space group, which was uniquely defined by the systematic absences in the data, was found (e.g. P1, P2(1), C2, and P21212). The data were integrated using the Bruker SAINT software program and scaled using the SADABS software program. Solution by direct methods (SHELXT) produced a complete phasing model compatible with the proposed structure.

All nonhydrogen atoms were refined anisotropically by full-matrix least-squares (SHELXL-2014). All hydrogen atoms were placed using a riding model. Their positions were constrained relative to their parent atom using the appropriate HFIX command in SHELXL-2014. Crystallographic data are summarized in tables below. The absolute stereochemistry was set to conform to previously studied samples of the same compound.

The single crystal X-ray crystallography data for Formula I Forms I-IV are summarized in Table 2A below. The single crystal X-ray crystallography data for Formula I Forms V-VIII are summarized in Table 2A-I below. The indexing data for Formula II Form I is summarized in Table 2C below. The single crystal X-ray crystallography data for the co-crystals of the present invention summarized in Table 2C below. The single crystal X-ray crystallography data for Formula III Forms I-III is summarized in Table 2D-I below. Data from further characterization of the crystals are summarized in Tables 3A and 3B below. Data from further characterization of the crystals are also summarized in Tables 3A-I and 3C-I below.

TABLE 2A

Single Crystal Data for Formula I Forms I-IV and Formula II Form I

| Form and Identification | Solvent | Solvent in lattice | Density (g/cm³) | Unit Cell Dimensions | | | | | |
|---|---|---|---|---|---|---|---|---|---|
| | | | | Distance (Å) | | | Angle (°) | | |
| | | | | a | b | c | α | β | γ |
| Formula I Form I | IPAc | none | 1.609 | 11.4498 (4) | 8.4767 (3) | 19.9163 (8) | 90 | 106.286 (2) | 90 |
| Formula I Form II | IPAc | 0.125 mole water | 1.537 | 8.5226 (7) | 26.934 (2) | 8.6861 (8) | 90 | 101.862 (2) | 90 |

TABLE 2A-continued

Single Crystal Data for Formula I Forms I-IV and Formula II Form I

| Form and Identification | Solvent | Solvent in lattice | Density (g/cm³) | Unit Cell Dimensions | | | | | |
|---|---|---|---|---|---|---|---|---|---|
| | | | | Distance (Å) | | | Angle (°) | | |
| | | | | a | b | c | α | β | γ |
| Formula I Form III | MIBK | none | 1.537 | 18.002 (2) | 10.9517 (12) | 20.687 (2) | 90 | 107.770 (4) | 90 |
| Formula I Form IV | methanol | 0.67 mole water | 1.484 | 29.948 (2) | 16.5172 (9) | 13.2051 (8) | 90 | 108.972 (4) | 90 |

TABLE 2A-I

Single Crystal Data for Formula I Forms V-VIII

| Form and Identification | Solvent | Solvent in lattice | Density (g/cm³) | Unit Cell Dimensions | | | | | |
|---|---|---|---|---|---|---|---|---|---|
| | | | | Distance (Å) | | | Angle (°) | | |
| | | | | a | b | c | α | β | γ |
| Formula I Form V | water | 0.5 mole water | 1.573 | 8.4993 (6) | 8.7290 (8) | 13.8619 (13) | 99.278 (5) | 101.427 (4) | 100.494 (4) |
| Formula I Form VI | methanol/ water | 0.5 mole water 0.5 mole methanol | 1.545 | 19.5163 (5) | 6.4593 (2) | 16.6066 (5) | 90 | 103.5680 (13) | 90 |
| Formula I Form VII | methanol | 1.08 mole water | 1.468 | 30.785 (12) | 16.685 (6) | 25.956 (10) | 90 | 108.189 (10) | 90 |
| Formula I Form VIII | methanol | None | 1.560 | 10.3242 (18) | 10.7826 (17) | 17.848 (3) | 90 | 105.578 (8) | 90 |

TABLE 2B

Indexing Data for Formula II Form I

| Form and Identification | Solvent | Unit Cell Dimensions | | | | | |
|---|---|---|---|---|---|---|---|
| | | Distance (Å) | | | Angle (°) | | |
| | | a | b | c | α | β | γ |
| Formula II Form I | methanol | 9.105 | 13.986 | 31.384 | 90 | 90 | 90 |

The single crystal X-ray crystallography data for Formula II Form I is summarized in Table 2B-I below.

TABLE 2B-I

Single Crystal Data for Formula II, Form I

| C42 H34 F6 N6 Na2 O10 Form and Identification | Acquisition | Space Group | Z | Unit Cell Dimensions | | | | | |
|---|---|---|---|---|---|---|---|---|---|
| | Temp. 100(2) K | P2₁2₁2₁ | 4 | | | | | | |
| | Solvent | Solvent in lattice | Density (Mg/m³) | Distance (Å) | | | Angle (°) | | |
| | | | | a | b | c | α | β | γ |
| Formula II Form I | Ethanol/ DMF | none | 1.614 | 8.9561 (10) | 13.9202 (14) | 31.115 (3) | 90 | 90 | 90 |

TABLE 2C

Single Crystal Data for Formula I Co-Crystals

| Form and Identification | Ratio Formula I:co-former | Solvent | Solvent in lattice (ratio) | Density (Mg/m³) | Unit Cell Dimensions Distance (Å) | | | Angle (°) | | |
|---|---|---|---|---|---|---|---|---|---|---|
| | | | | | a | b | c | α | β | γ |
| Formula I Citric Acid co-crystal | 1:2 | THF | None | 1.608 | 7.4315 (6) | 15.5755 (13) | 15.6856 (13) | 88.784 (2) | 77.029 (2) | 76.832 (2) |
| Formula I Fumaric acid co-crystal | 1:1 | THF | THF (0.375 mole) | 1.503 | 26.767 (5) | 8.2313 (14) | 24.089 (4) | 90 | 99.283 (4) | 90 |
| Formula I Oxalic Acid co-crystal | 1:1 | THF | None | 1.604 | 7.8562 (3) | 14.5031 (5) | 19.9756 (7) | 90 | 101.291 (2) | 90 |

TABLE 2D-1

Single Crystal Data for Formula III, Forms I-III

| Form and Identification | Solvent | Density (Mg/m³) | Unit Cell Dimensions Distance (Å) | | | Angle (°) | | |
|---|---|---|---|---|---|---|---|---|
| | | | a | b | c | α | β | γ |
| Formula III Form I | Ethanol/water | 1.498 | 32.0409 (11) | 10.2935 (4) | 15.4691 (7) | 90 | 90 | 90 |
| Formula III Form II | Acetonitrile/water | 1.336 | 32.0285 (17) | 10.3029 (7) | 15.5363 (10) | 90 | 90 | 90 |
| Formula III Form III | Methanol | 1.483 | 8.8412 (3) | 10.8837 (4) | 13.9107 (5) | 71.3620 (10) | 76.343 (2) | 82.943 (2) |

TABLE 3A

Crystal Data and Structure Refinement for Formula I Forms I-IV

| Property | Formula I Form I | Formula I Form II | Formula I Form III | Formula I Form IV |
|---|---|---|---|---|
| Empirical formula | $C_{21}H_{18}F_3N_3O_5$ | $C_{21}H_{18.25}F_3N_3O_{5.12}$ | $C_{21}H_{18}F_3N_3O_5$ | $C_{21}H_{19.3}F_3N_3O_{5.67}$ |
| Formula weight | 449.38 | 451.64 | 449.38 | 461.46 |
| Temperature | 100(2) K | 200(2) K | 100(2) K | 100(2) K |
| Wavelength | 1.54178 Å | 0.71073 Å | 1.54178 Å | 1.54178 Å |
| Crystal system | Monoclinic | Monoclinic | Monoclinic | Monoclinic |
| Space group | P2(1) | P2(1) | P2(1) | C 2 |
| Volume | 1855.44(12) Å³ | 1951.3(3) Å³ | 3884.0(8) Å³ | 6177.3(7) Å³ |
| Z | 4 | 4 | 8 | 12 |
| Density (calculated) | 1.609 g/cm³ | 1.537 Mg/m³ | 1.537 g/cm³ | 1.484/m³ |

TABLE 3A-I

Crystal Data and Structure Refinement for Formula I Forms V-VIII

| Property | Formula I Form V | Formula I Form VI | Formula I Form VII | Formula I Form VIII |
|---|---|---|---|---|
| Empirical formula | $C_{21}H_{20}F_3N_3O_{5.5}$ | $C_{21.5}H_{20}F_3N_3O_6$ | $C_{21}H_{18}F_{13}N_{13}O_{6.08}$ | $C_{21}H_{18}F_3N_3O_5$ |
| Formula weight | 459.40 | 473.40 | 466.72 | 449.38 |
| Temperature | 100(2) K | 200(2) K | 100(2) K | 100(2) K |
| Wavelength | 0.71073 Å | 1.54178 Å | 0.71073 Å | 0.71073 Å |
| Crystal system | Triclinic | Monoclinic | Monoclinic | Monoclinic |
| Space group | P2(1) | P2(1) | P2(1) | C 2 |
| Volume | 970.18(14) Å³ | 2035.03(10) Å³ | 12666(8) Å³ | 1913.9(6) Å³ |
| Z | 2 | 4 | 24 | 4 |
| Density (calculated) | 1.573 Mg/m³ | 1.545 Mg/m³ | 1.468 Mg/m³ | 1.560 Mg/m³ |

TABLE 3B

Crystal Data and Structure Refinement for Formula I Co-Crystals

| Property | Formula I Citric Acid co-crystal | Formula I Fumaric Acid co-crystal | Formula I Oxalic Acid co-crystal |
|---|---|---|---|
| Empirical formula | $C_{33}H_{34}F_3N_3O_{19}$ | $C_{26.50}H_{25}F_3N_3O_{9.38}$ | $C_{23}H_{20}F_3N_3O_9$ |
| Formula weight | 833.63 | 592.49 | 539.42 |
| Temperature | 100(2) K | 100(2) K | 150(2) K |
| Wavelength | 0.71073 Å | 0.71073 Å | 0.71073 Å |
| Crystal system | Triclinic | Monoclinic | Monoclinic |
| Space group | P1 | C2 | P2(1) |
| Volume | 1721.9(2) Å$^3$ | 5237.9(16) Å$^3$ | 2231.95(14) Å$^3$ |
| Z | 2 | 8 | 4 |
| Density (calculated) | 1.608 Mg/m$^3$ | 1.503 Mg/m$^3$ | 1.604 g/cm$^3$ |

TABLE 3C-I

Crystal Data and Structure Refinement for Formula III Form I, Formula III Form II (Dimer), and Formula III, Form III

| Property | Formula III Form I | Formula III Form II | Formula III Form III |
|---|---|---|---|
| Empirical formula | $C_{21}H_{17}F_3KN_3O_{10.5}$ | $C_{42}H_{34}F_6K_2N_6O_{13.50}$ | $C_{23}H_{23}F_3KN_3O_7$ |
| Formula weight | 575.47 | 1030.95 | 549.54 |
| Temperature | 100(2) K | 100(2) K | 100(2) K |
| Wavelength | 0.71073 Å | 0.71073 Å | 0.71073 Å |
| Crystal system | Orthorhombic | Orthorhombic | Triclinic |
| Space group | P 21 21 2 | P 21 21 2 | P 1 |
| Volume | 5101.9(4) Å$^3$ | 5126.8(6) Å$^3$ | 1230.86 (8) Å$^3$ |
| Z | 8 | 4 | 2 |
| Density (calculated) | 1.498 Mg/m$^3$ | 1.336 Mg/m$^3$ | 1.483 Mg/m$^3$ |

In certain embodiments of the invention, Formula III is hydrated. In certain embodiments, Formula III is hydrated with five to six water molecules.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed:

1. A method for treating an HIV infection in a human in need thereof, comprising administering to the human a therapeutically effective amount of a crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the crystalline form is Form I.

2. The method of claim 1 wherein the crystalline form is characterized by an x-ray powder diffraction (XRPD) pattern having peaks at about 13.1°, 16.2°, and 20.6° 2-θ±0.2° 2-θ.

3. The method of claim 2 wherein the x-ray powder diffraction (XRPD) pattern has further peaks at about 25.0° and 27.4° 2-θ±0.2° 2-θ.

4. The method of claim 3 wherein the x-ray powder diffraction (XRPD) pattern has further peaks at about 9.3° and 10.5° 2-θ±0.2° 2-θ.

5. The method of claim 4 wherein the x-ray powder diffraction (XRPD) pattern has further peaks at about 11.4°, 13.9°, 17.4°, and 22.3° 2-θ±0.2° 2-θ.

6. The method of claim 1 wherein the crystalline form is characterized by an x-ray powder diffraction (XRPD) pattern substantially as set forth in FIG. 1.

7. The method of claim 1 wherein the crystalline form is characterized by differential scanning calorimetry (DSC) pattern substantially as set forth in FIG. 7.

8. The method of claim 1 wherein the crystalline form is characterized by a dynamic vapor sorption (DVS) pattern substantially as set forth in FIG. 13.

9. A method for treating an HIV infection in a human in need thereof, comprising administering to the human a pharmaceutical composition comprising a therapeutically effective amount of a crystalline form of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, wherein the crystalline form is Form I, and a pharmaceutically acceptable carrier or excipient.

10. The method of claim 9 wherein the pharmaceutical composition further comprises one to three additional therapeutic agents.

11. The method of claim 10, wherein the additional therapeutic agents are each anti-HIV drugs.

12. The method of claim 10, wherein the additional therapeutic agents are each independently selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, pharmacokinetic enhancers, and other drugs for treating HIV.

13. The method of claim 12, wherein at least two of the additional therapeutic agents are each HIV nucleotide or nucleoside inhibitors of reverse transcriptase.

14. The method of claim 9, wherein the pharmaceutical composition further comprises tenofovir disoproxil fumarate and emtricitabine.

15. The method of claim 9, wherein the pharmaceutical composition further comprises tenofovir alafenamide and emtricitabine.

16. The method of claim 9, wherein the pharmaceutical composition further comprises tenofovir alafenamide hemifumarate and emtricitabine.

17. The method of claim 9, wherein the pharmaceutical composition is in a unit dosage form.

18. The method of claim 17, wherein the unit dosage form is a tablet.

19. The method of claim 9, wherein the pharmaceutical composition further comprises tenofovir alafenamide fumarate and emtricitabine.

* * * * *